(12) United States Patent
Chen

(10) Patent No.: US 6,573,096 B1
(45) Date of Patent: Jun. 3, 2003

(54) COMPOSITIONS AND METHODS FOR INHIBITION OF CANCER INVASION AND ANGIOGENESIS

(75) Inventor: Wen-Tien Chen, Stony Brook, NY (US)

(73) Assignee: The Research Foundation at State University of New York, Stony Brook, NY (US)

( * ) Notice: Subject to any disclaimer, the term of this patent is extended or adjusted under 35 U.S.C. 154(b) by 0 days.

(21) Appl. No.: 09/541,785

(22) Filed: Apr. 3, 2000

Related U.S. Application Data

(60) Provisional application No. 60/193,987, filed on Apr. 1, 2000.

(51) Int. Cl.[7] .................................................. C12N 5/00
(52) U.S. Cl. ..................... 435/326; 435/327; 435/330; 435/338
(58) Field of Search .......................... 530/388.1, 388.15, 530/388.26, 388.8, 389.1, 389.7, 391.3, 391.7; 424/130.1, 133.1, 135.1, 146.1, 155.1; 435/326, 327, 330, 338

(56) References Cited

U.S. PATENT DOCUMENTS

| | | | |
|---|---|---|---|
| 5,092,885 A | 3/1992 | Yamada et al. | |
| 5,221,622 A | 6/1993 | Chen | |
| 5,942,385 A | 8/1999 | Hirth | |
| 5,980,896 A | 11/1999 | Hellstrom et al. | |

FOREIGN PATENT DOCUMENTS

WO   WO 96/38550   * 12/1996

OTHER PUBLICATIONS

Auerbach et al., Pharmac. Ther. 63:265–311, 1994.*
Jain, Cancer and Metastasis Reviews 9:253–266, 1990.*
Seaver, Genetic Engineering News, 14/14:10 and 21, 1994.*
Harris et al. , Trends in Biotechnology 11:42–44, 1993.*
Gura, Science 278:1041–1042, 1997.*
Liddell et al. , pp. 25–44 in Antibody Technology, Bios Scientific Publishers, Oxford, 1995.*
Hartel–Schenk et al. ,Eur. J. Biochem. 196:349–355, 1991.*
Reinhold et al. , Immunobiology, 188:403–414, 1993.*
Van den Oord, British Journal of Dermatology, 138:615–621, 1998.*
Cheng et al. , The Journal of Biological Chemistry 273/37:24207–24215, 1998.*
Mattern et al., Immunobiology 178(1/2):110, Abstract H.12, 1988.*

Heins et al., "Mechanism of proline–specific proteinases: (I) substrate specificity of dipeptidyl peptidase IV from pig kidney and proline–specific endopeptidase from *Flavobacterium meningosepticum*", *Biochimica et Biophysica Acta* 954 (1988) 161–169.
Wen–Tien Chen and Jaw–Yuan Wang, "Specialized Surface Protrusions of Invasive Cells, Invadopodia and Lamellipodia, Have Differential MT1–MMP, MMP–2, and TIMP–2 Localization", Jun. 30, 1999, *Annals of the New York Acad. Of Sciences*, vol. 878, pp. 361–371.
Susette C. Mueller et al., "A Novel Protease–docking Function of Integrin at Invadopodia", *The Journal of Biological Chemistry*, vol. 274, No. 35, Issue of Aug. 27, pp. 24947–24952, 1999.
Donald Ingber and Judah Folkman, "Inhibition of Angiogenesis Through Modulation of Collagen Metabolism", *Laboratory Investigation*, vol. 59, No. 1, p. 44, 1988.
Marsha A. Moses et al., "Identification of an Inhibitor of Neovascularization from Cartilage", *Science*, vol. 248, p. 1408. (1990).
Christine H. Blood and Bruce R. Zetter, "Tumor interactions with the vasculature: angiogenesis and tumor metastasis", *Biochimica et Biophysica Acta*, 1032 (1990) 89–118.
Leslie A. Goldstein and Wen–Tien Chen, "Identification of an Alternatively Spliced Seprase mRNA That Encloses a Novel Intracellular Isoform", *The Journal of Biological Chemistry*, vol. 275, No. 4 Issue of Jan. 28, pp. 2554–2559, 2000.

* cited by examiner

*Primary Examiner*—Sheela Huff
(74) *Attorney, Agent, or Firm*—Hoffman & Baron, LLP

(57) ABSTRACT

The invention provides antibodies to a membrane protease complex, consisting of two homodimers of seprase and dipeptidyl peptidase IV (DPPIV), obtained from human cell membranes. The antibodies specifically bind the DPPIV protease of the seprase-DPPIV complex that resides on cell surface invadopodia at the leading edge of angiogenic endothelia, migratory fibroblasts, and invading cancer cells, while failing to react with resting cells in adjacent human tissues and blood vessels. These antibodies block interaction of collagen matrix with the seprase-DPPIV complex in the invasive cells during angiogenesis and cancer spreading but not that with other endothelia or tumor cells. The invention further provides methods of using DPPIV antagonists to inhibit capillary sprouting, angiogenesis and cancer invasion in tumor tissues and metastases. Also provided are therapeutic compositions comprising DPPIV antagonists.

5 Claims, 16 Drawing Sheets

(3 of 16 Drawing Sheet(s) Filed in Color)

FAP1 + 2     FAP11 + 4     GPDH

DPPF1 + DPPR2

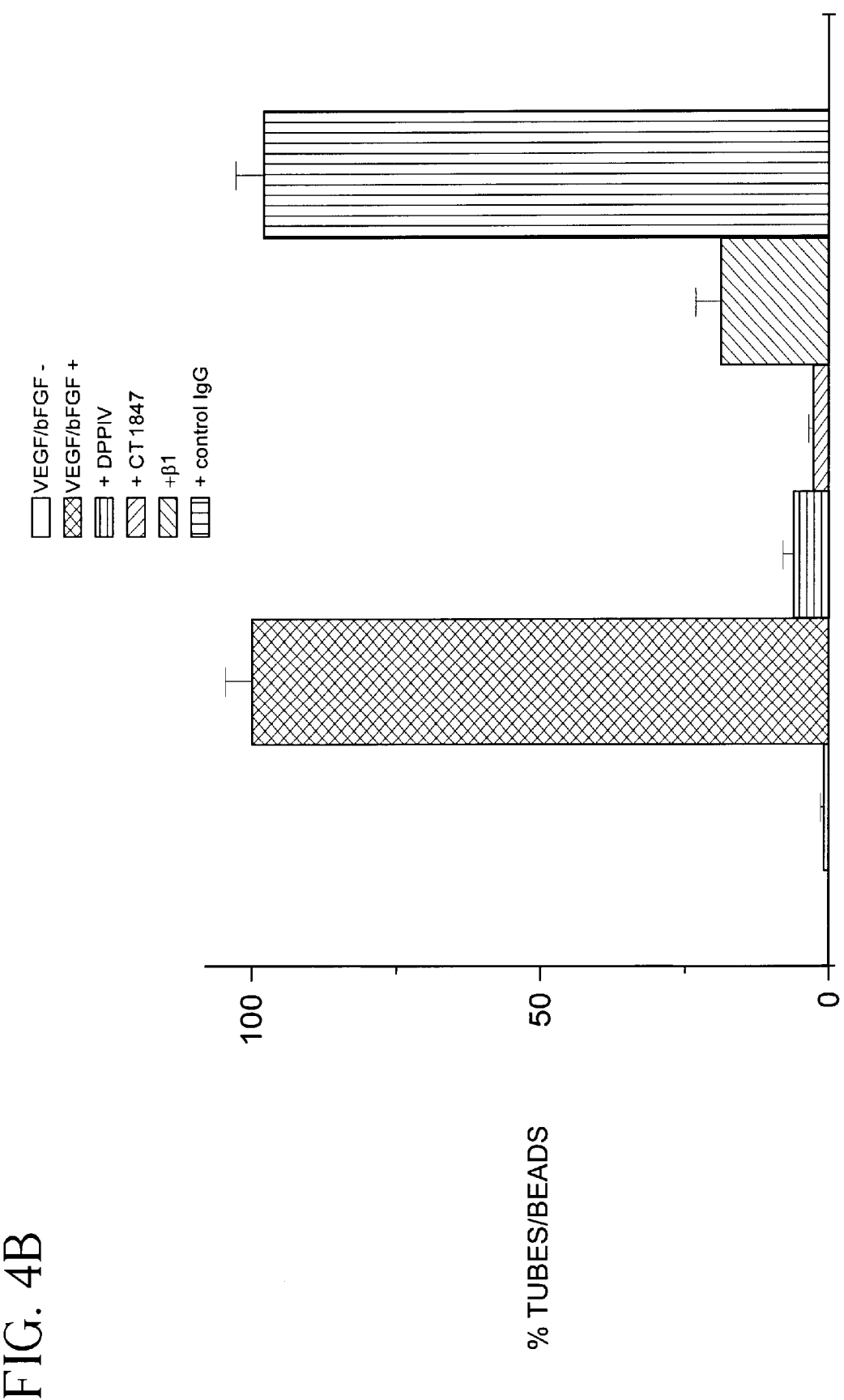

COMPOSITIONS AND METHODS FOR INHIBITION OF CANCER INVASION AND ANGIOGENESIS

This application claims the benefit of provisional application U.S. Serial No. 60/193,987 filed Apr. 1, 2000.

This work was supported by grants from one or more of the following: U.S. Public Health Service, National Cancer Institute and The National Institute of Aging. The government may have certain rights to this invention.

FIELD OF THE INVENTION

The present invention relates generally to the field of medicine, and relates specifically to angiogenesis and metastasis of cancer tissues. Specifically the invention relates to the use of antagonists of the serine integral membrane protease, dipeptidyl peptidase IV (DPPIV also known as CD26).

BACKGROUND OF THE INVENTION

Growth of new blood vessels (angiogenesis) plays a key role in tissue repair and in cancer progression. The invasion of cells into a connective tissue barrier during angiogenesis requires remodeling of the extracellular matrix (ECM) by migratory cells (Martin, 1997). In cancer invasion such cellular activities occur on membrane protrusions invadopodia (Chen, 1979) which exhibit dynamic membrane mobility, ECM adhesion and degradation. Thus, cellular invasion is an important process for cancer metastasis (Stetler-Stevenson et al., 1993). Several classes of proteases including matrix metalloproteinases (MMPs), serine proteases, cysteine proteases (cathepsin B and cathepsin L), and aspartic acid proteases (cathepsin D) can degrade proteins in the ECM (Chen, 1992). And invading cancer cells possess ECM degrading proteolytic enzymes that are concentrated at specialized plasma membrane protrusions, termed invadopodia (Chen et al., 1994). Recent studies showed that integral membrane proteases might contribute significantly to ECM degradation and ultimately cancer invasion by virtue of their location at invadopodia (Monsky and Chen, 1993).

Recent evidence has demonstrated the involvement of serine-integral membrane roteases (SIMP), including dipeptidyl peptidase IV (DPPIV)/CD26 and seprase, in cell surface proteolysis (Chen, 1996). SIMP members are type II transmembrane proteins, with cytoplasmic tails that contain 6 amino acids (a.a.) followed by a 20 a.a. (seprase) or 22 a.a. (DPPIV) transmembrane domain at the N-terminus and a stretch of 200 a.a. at the C-terminus that constitutes a catalytic region with the catalytic serine in a non-classical orientation (Goldstein et al., 1997; Pineiro-Sanchez et al., 1997).

DPPIV specifically removes N-terminal dipeptides from oligo-peptides, which include Neuro-Peptide Y and other peptide hormones, with either L-proline, L-hydroxyproline, or L-alanine at the penultimate position (Heins et al., 1988, Walter et al., 1980). DPPIV has been shown to be an adhesion receptor for collagen (Bauvois, 1988; Hanski et al., 1988; Loster et al., 1995) or fibronectin (Cheng et al., 1998; Johnson, et al., 1993; Piazza et al., 1989). In addition, a recent report showed that DPPIV also possesses a seprase-like gelatinase activity and therefore endopeptidase activity (Bermpohl et al., 1998), suggesting its involvement in collagen degradation. DPPIV is expressed constitutively on brush border membranes of intestine and kidney epithelial cells (Yaron and Naider, 1993; Morimoto and Schlossman, 1994).

Seprase, originally identified as a 170 kDa membrane-bound gelatinase is expressed on invadopodia of highly aggressive melanoma LOX cells (Aoyama and Chen, 1990; Mueller et al., 1999; Monsky et al., 1994). The active enzyme is a homodimer of 97 kDa subunits, which are proteolytically inactive (Pineiro-Sanchez et al., 1997). Analysis of the deduced amino acid sequence from a cDNA that encodes the 97 kDa subunit (Goldstein et al., 1997) revealed that it is homologous to DPPIV, and is essentially identical to fibroblast activation protein α (FAPα) (Scanlan et al., 1994), which is expressed on reactive stromal fibroblasts of epithelial cancers and healing wounds (Garin-Chesa et al., 1990). In addition, DNA and protein analysis of embryonic tissues has suggested potential additional members of SIMP (Bermpohl et al., 1998).

A growing body of evidence indicates that angiogenesis is essential to the progression of cancer. Angiogenesis is the sprouting of new capillaries from preexisting blood vessels. Normally, angiogenesis in mammals is confined to the reproductive system, embryogenesis and development, and repair after injury. However, angiogenesis can also occur in pathological conditions such as cancer, retinal neovascularization, neovascularization in atherosclerotic plaques, hemangiomas, arthritis, and psoriasis. See Folkman, 1995. Without vascularization, tumors may remain for years as small (less than a few millimeters) asymptomatic lesions. Weidner et al. (1991). Angiogenesis allows the cancer cells access to the circulatory system. The new blood vessels provide a gateway for cancer cells to enter the circulation and metastasize to distant sites (Folkman 1990; Klagsbrunn and Soker, 1993).

As in cancer cell invasion, angiogenesis involves matrix degradation by migrating endothelial cells at the invasion front; proteases including matrix metalloproteases (MMPs) (Hiraoka et al., 1998; Brooks et al., 1998) and plasminogen activators (Pepper et al., 1993) are essential but novel membrane-bound proteases active at sites of angiogenesis are yet to be defined.

Several approaches for inhibition of angiogenesis have been proposed as useful therapies for restricting tumor growth. These include inhibition of angiogenesis by (1) inhibition of release of "angiogenic molecules" such as VEGF (Vascular endothelial growth factor) and basic.FGF (fibroblast growth factor), (2) neutralization of angiogenic molecules, such as by use of anti-b.FGF antibodies, (3) targeted inhibition on .alpha..sub.v .beta..sub.3 integrin, and (4) inhibition of the endothelial cell response to angiogenic stimuli. This latter strategy has received attention, and Folkman et al., Cancer Biology, 3:89–96 (1992), have described several endothelial cell response inhibitors, including collagenase inhibitor, basement membrane turn-over inhibitors, angiostatic steroids, fungal-derived angiogenesis inhibitors, platelet factor 4, thrombospondin, arthritis drugs such as D-penicillamine and gold thiomalate, vitamin D.sub.3 analogs, alpha-interferon, and the like that might be used to inhibit angiogenesis.

Monoclonal antibodies (MAbs) to human tumor-associated differentiation antigens offer promises for the "targeting" of various antitumor agents such as radioisotopes, chemotherapeutic drugs, and toxins. [Order, in "Monoclonal Antibodies for Cancer Detection and Therapy", Baldwin and Byers, (eds.),London, Academic Press (1985)].

In addition, some monoclonal antibodies have the advantage of killing tumor cells via antibody-dependent cellular cytotoxicity (ADCC) or complement-dependent cytotoxicity (CDC) in the presence of human effector cells or serum [Hellstrom et al., Proc. Natl. Acad. Sci. USA 83:7059–7063 (1986)], and there are a few monoclonal antibodies that have a direct antitumor activity which does not depend on any host component [Drebin et al., Oncogene 2:387–394 (1988)].

For additional proposed inhibitors of angiogenesis, see Blood et al., Bioch. Biophys. Acta., 1032:89–118 (1990) for a general review of angiogenesis and tumor metastasis; also Moses et al., Science, 248:1408–1410 (1990) describes a protein inhibitor of angiogenesis derived from cartilage; and Ingber & Folkman, Lab. Invest. 59:44–51 (1988) describes inhibition of angiogenesis through modulation of collagen metabolism.

U.S. Pat. No. 5,092,885, of Yamada et al. discloses laminin peptides with angiogenesis-blocking activity. U.S. Pat. No. 5,112,946 of Maione et al. discloses modified PF4 compositions as inhibitors of angiogenesis.

U.S. Pat. No. 5,192,744, discloses human thrombospondin for use as an inhibitor of angiogenesis. U.S. Pat. No. 5,202,352 discloses intravascular embolizing agents containing angiogenesis inhibiting substances in oils, emulsions or suspensions. U.S. Pat. No. 5,766,591 discloses antagonists of vitronectin alpha.sub.v.beta.sub.3 as angiogenesis inhibitors.

U.S. Pat. No. 5,980,896 of Hellstrom et al. discloses antibodies and immunoconjugates reactive with human carcinomas and is especially useful in practicing the full scope of the present invention. Among the disclosed compositions and methods which are especially applicable to the present invention are: chimeric antibodies, immunoconjugates thereof and their methods of preparation and use; and anti-tumor drugs, cytotoxins, radioactive agents and enzymes useful in immunoconjugate compositions. The text of U.S. Pat. No. 5,980,896 is hereby incorporated by reference in its entirety.

There is still a need, however for novel and more effective anti-angiogenesis therapies for use alone or in combination with one or more of the currently available therapies for treatment of growth and proliferative disorders involving angiogenesis.

SUMMARY OF THE INVENTION

The invention provides monospecific antibodies which specifically bind an epitope of a human DPPIV (dipeptidyl peptidase IV/CD26) and inhibits angiogenesis.

Also provided are bispecific antibodies with binding specificity for two epitopes, one of which is an epitope of DPPIV. The bispecific antibodies of the present invention include those in which the second epitope bound is an epitope of seprase, MT1-MMP, MMP-2 or $\alpha(3)\beta(1)$-integrin.

The present invention further provides immunoconjugates comprising a monospecific or a bispecific antibody which specifically binds an epitope of human DPPIV (dipeptidyl peptidase IV/CD26) and inhibits angiogenesis, joined to a therapeutic agent.

In yet another aspect the invention provides pharmaceutical compositions for inhibiting angiogenesis comprising an effective amount of an antibody which specifically binds an. epitope of a human DPPIV (dipeptidyl peptidase IV/CD26) and inhibits angiogenesis, the antibody being formulated in a pharmaceutically acceptable carrier.

In yet another aspect the invention provides pharmaceutical compositions for inhibiting angiogenesis comprising an effective amount of an immunoconjugate of an antibody which specifically binds an epitope of a human DPPIV (dipeptidyl peptidase IV/CD26) and inhibits angiogenesis, the antibody being formulated in a pharmaceutically acceptable carrier.

The present invention yet further provides a method of treating a patient suffering from a growth or proliferative disorder involving angiogenesis, comprising administering to the site of angiogenesis an effective amount of an antibody which specifically binds an epitope of a human DPPIV (dipeptidyl peptidase IV/CD26) and inhibits angiogenesis.

In yet another aspect the present invention provides a method of treating a patient suffering from a growth or proliferative disorder involving angiogenesis, comprising administering to the site of angiogenesis an effective amount of an immunoconjugate which specifically binds an epitope of a human DPPIV (dipeptidyl peptidase IV/CD26) and inhibits angiogenesis.

In a further aspect the present invention provides continuous cell lines which produce monospecific antibodies that specifically bind an epitope of a human DPPIV (dipeptidyl peptidase IV/CD26) and thereby inhibit angiogenesis.

BRIEF DESCRIPTION OF THE FIGURES

The file of this patent contains at least one figure executed in color. Copies of this patent with color figure(s) will be provided by the Patent and Trademark Office upon request and payment of the necessary fee.

Figure 1:
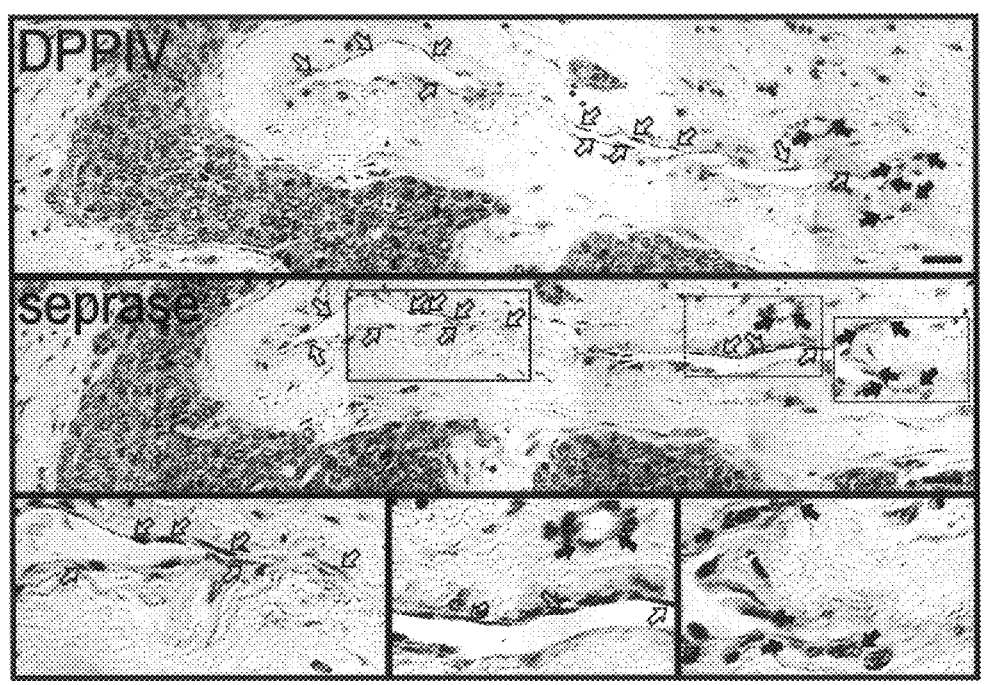
FIG. 1. Seprase and DPPIV expression in the endothelial cells of sprouting vessels but not in differentiated vessels in human malignant breast carcinoma. Both seprase (middle panel) and DPPIV (upper panel) are present in the endothelial cells of sprouting microvessels (brown stains indicated by black solid arrows) but not in endothelia of adjacent vessels (open arrows). Adjacent to microvessels are cell clusters of invasive breast carcinoma that stain positively for seprase and DPPIV. The bottom panel is an expanded view of seprase staining of vessels. Paraffin sections of breast carcinoma tissue were stained with the anti-seprase mAb D28 or the anti-DPPIV mAb E26. Bar=100 µm.

Minus reverse transcriptase controls are shown in lanes marked "RT". Similar amounts of glyceraldehyde-3-phosphate-dehydrogenase mRNA were detected in both the confluent and sparse HUVEC (Lanes marked GPDH). These results suggest that the increased expression of seprase detected in sparse HUVEC is not due to an upregulation in the seprase mRNA level; but instead is due to increased translational efficiency of the seprase mRNA and/or increased stability of seprase itself. e, Detection of DPPIV RNA. RT-PCR was carried out on total RNA from confluent (+) and sparse (−) HUVEC using oligonucleotide primers DPPF1+DPPR2 that correspond to nucleotide positions #24–43 (5' UTR) and #2798–2781 (3' UTR) in human DPPIV cDNA. f–g, Immunofluorescence distribution of seprase and DPPIV in migratory HUVEC stimulated by wounding (indicated by arrows) of the monolayer (central panels). The wound monolayer was stained three hours later with antibodies against DPPIV (E26) and β1 (C27) or seprase (D28) and β1 (C27), respectively. Bar=10 μm. h, Morphology of HUVEC migration at time 0 and 24 hours after wounding of the monolayer (panels marked 24 hr). The wound was closed within 24 hours but cell migration could be blocked by mAbs E19 or E26 against DPPIV. i, Dose-dependent inhibition of cell migration by inhibitory mAb E19 (against DPPIV;—□ open squares) and C27 (β1; open triangles) but not by control mAb E3 against DPPIV (DPPIV solid triangles) or C37 (against cell surface glycoprotein gp90; solid circles). Three experiments of 4 h monolayer wound models were carried out for each antibody. Cell migration was quantified by measuring the areas of cell advancement from the original wound edge. The values are mean±SD. j, Time-course of antibody inhibition of cell migration. All antibodies, mAb E19 (against DPPIV;—□ open squares), C27 (β1; open triangles), E3 (DPPIV solid triangles), C37 (glycoprotein gp90; solid circles), or buffer alone (Control; solid diamonds) were applied at 5 μg per ml. Experimental conditions were the same as panel i above.

FIGS. 3A–D. Inhibition of endothelial tube formation by a mAb to DPPIV. a, Morphology of HUVEC tube formation in Matrigel assay (Control). It could be blocked by mAb E19 or E26 (DPPIV). Bar=100 μm. b, Inhibition of endothelial tube formation. All antibodies, mAb E26 (against DPPIV), C27 (β1), E3 or C37 (control IgG), or buffer alone (Control) were applied at 5 μg per ml prior to tube formation when cells adhered to Matrigel. The matrix metalloprotease inhibitor CT1847 was added at 10 nM in the presence of 0.01% DMSO and 0.01% DMSO was used as vehicle control (+DMSO). Three experiments for each antibody or inhibitor were used in this plot. Tube formation was quantified by measuring the areas of tubes in each well. The values are mean±SD. c, Inhibition of preexisting endothelial tubes by antibodies to DPPIV and β1 or the matrix metalloprotease inhibitor CT1847. Experimental conditions were identical to above except antibodies and inhibitors were applied after tubes were formed. d, Immunofluorescent distribution of seprase in migratory HUVEC (indicated by arrow) from a tube in Matrigel. The HUVEC culture (phase contrast image shown in the left panel) was stained with antibodies against seprase (D8) (right panel), respectively. Bar=10 μm.

Figure 4A:
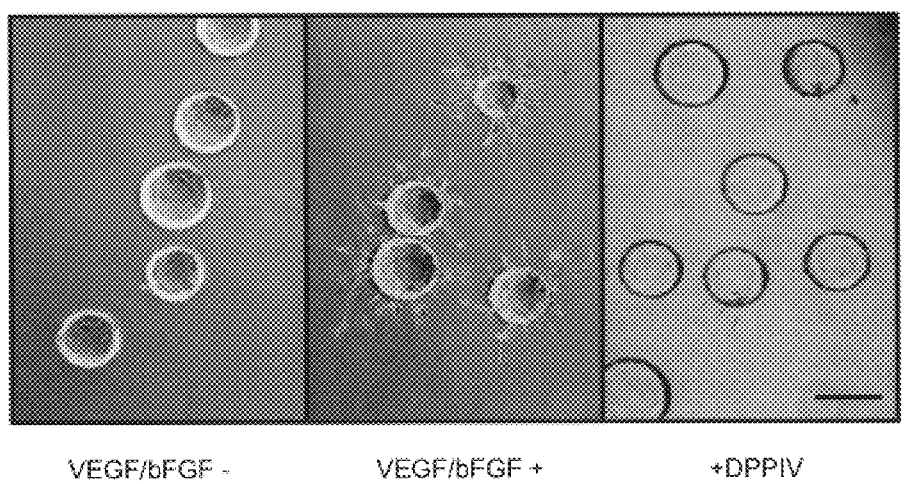

FIGS. 4A and B. Inhibition of human angiogenesis in vitro by a mAb to DPPIV. a, Morphology of VEGF- and bFGF-induced HDMEC capillary sprouts and capillary networks (VEGF/bFGF–and +), which could be blocked by mAb E19 or E26 (+DPPIV). Bar=200 μm. b, Inhibition of HDMEC capillary sprouts. All antibodies, mAb E26 (+DPPIV), mAb C27 (+β1), and E3 or C37 (+control IgG), were applied at 20 μg per ml to impregnated fibrin gels. The matrix metalloprotease inhibitor CT1847 was added at 40 nM in the presence of 0.01% DMSO; 0.01% DMSO was used as vehicle control. Three experiments for each antibody or inhibitor were performed in this plot. Capillary sprouting was quantified by measuring the number of tubes and beads in each well. The ratio of tubes/beads occurring with VEGF/bFGF+ samples was arbitrarily set at 100%. The values are mean±SD.

Figure 5:
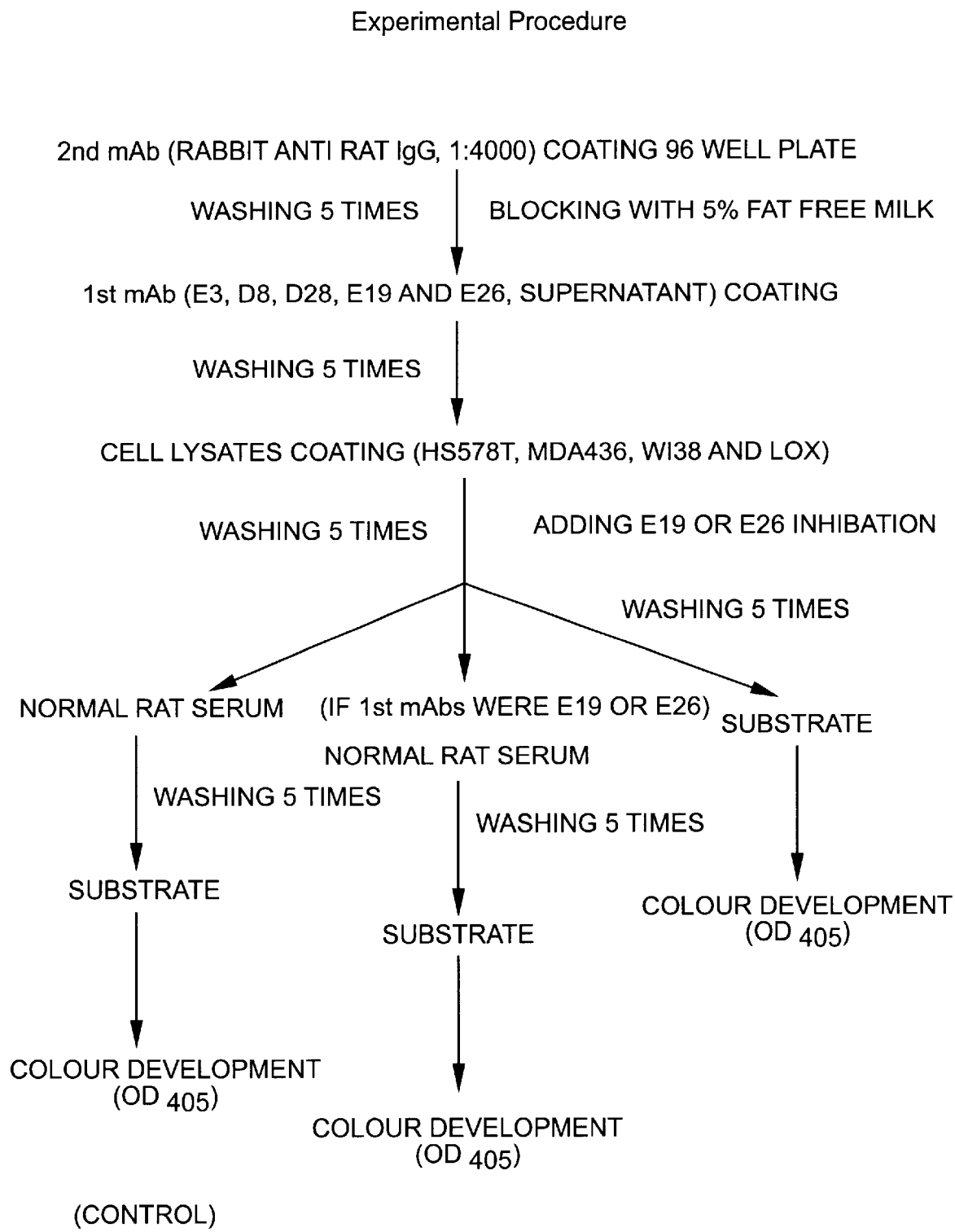
Figure 6A:
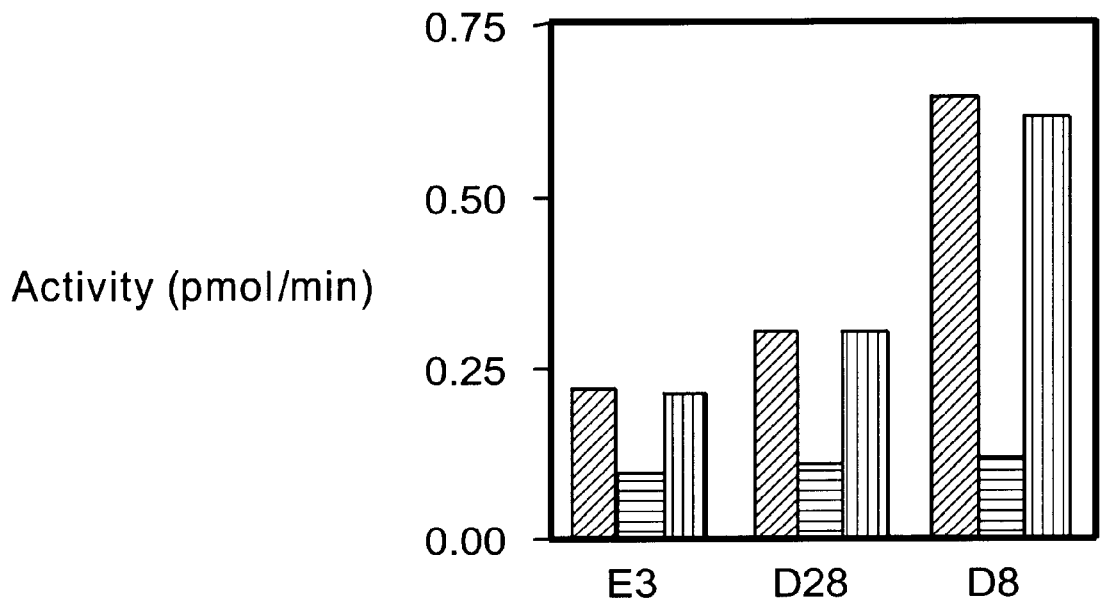
Figure 6B:
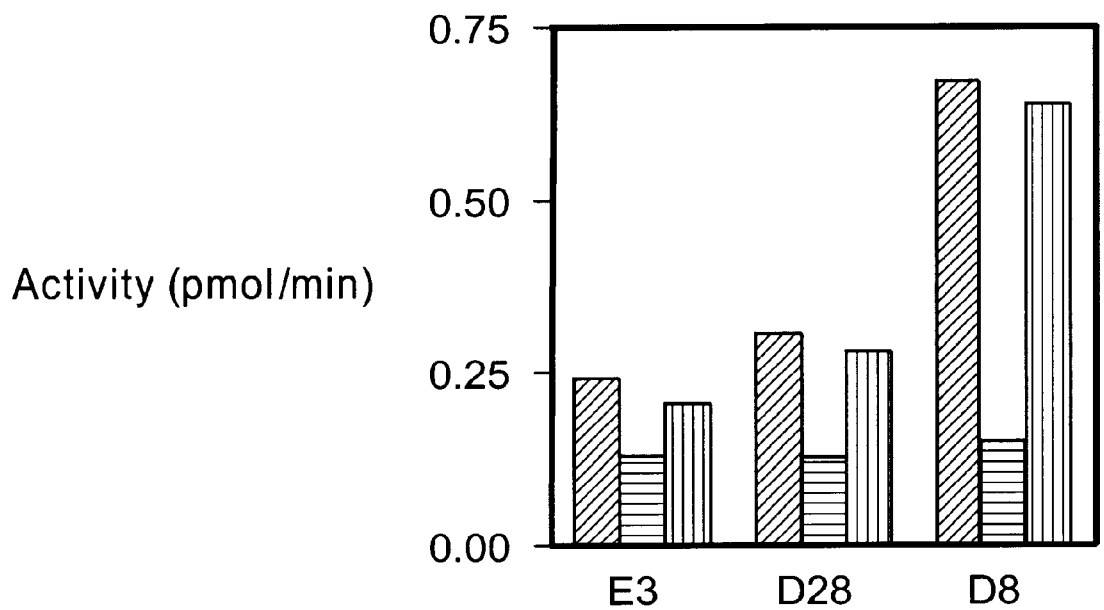
Figure 6C:
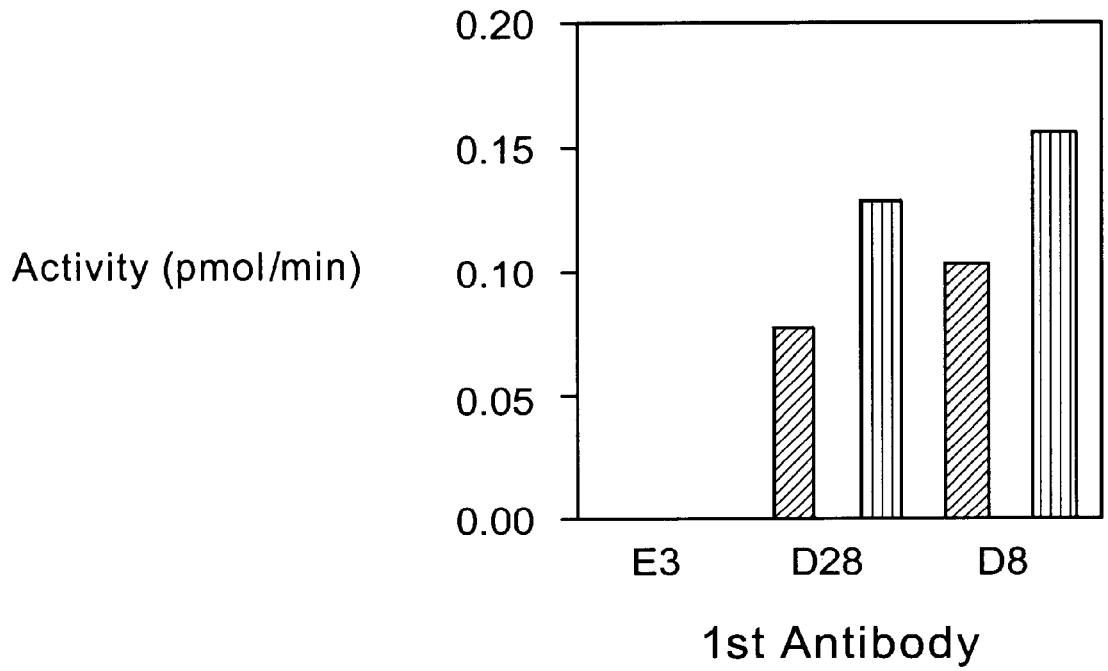
Figure 6D:
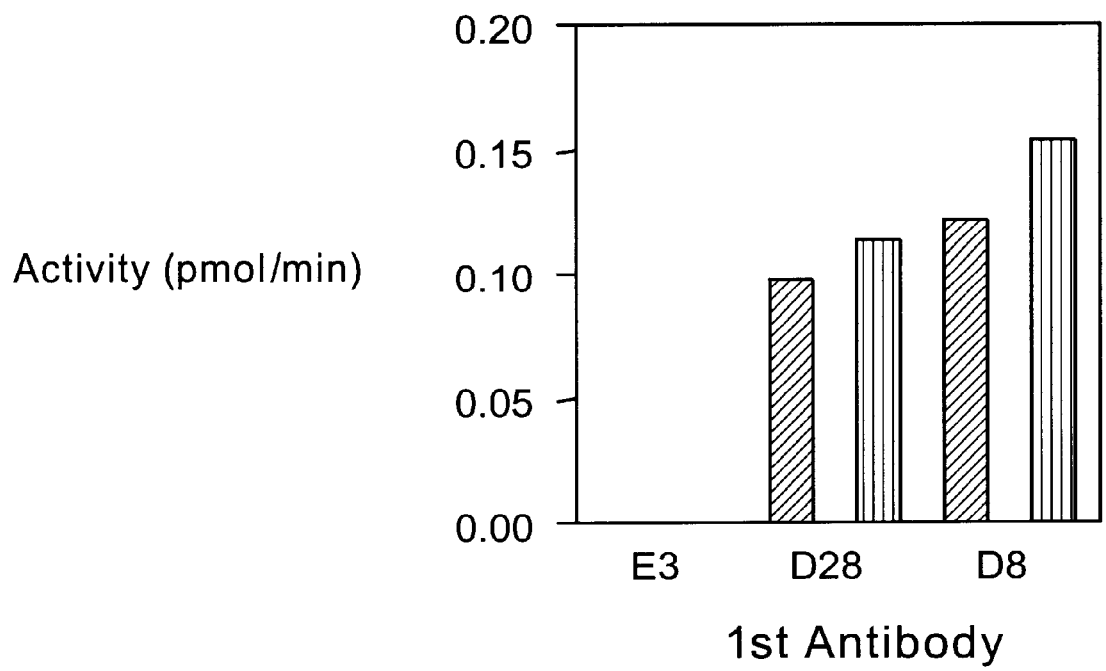

FIG. 5. Experimental procedure for DPPIV/Seprase antigen capture and inhibition assay. Plates were coated with rabbit anti-rat IgG (1:4000 dilution) in blocking buffer (5% fat free milk in 1×PBS)and washed (in washing buffer: 0.05% Tween-20 in 1×PBS). The wells were then incubated with the capture antibody (E3-anti-DPPIV, D8-anti-seprase, D28-anti-seprase, or normal rat serum=supernatant). Alternatively, wells were then incubated with an inhibitory anti-DPPIV antibody E19, or E26 as capture antibody. Wells were washed 5× and incubated with second antibody and again washed 5×. Cell lysates (HS578T, MDA436, WI38 or LOX) or lysates pretreated with anti-DPPIV antibody E19 or E26 were incubated in coated wells, washed and assayed for DPPIV peptidase activity. Antibody reactions were carried out at 37° C. for 4 hrs. DPPIV peptidase assays were developed with chromogenic substrate Gly-Pro-pNA (2.15 mM) or fluorogenic substrate Gly-Pro-AMC (14.6 mM).

FIGS. 6A–D: HS578T and LOX cell lysate DPPIV activity inhibition by mAb E19 or mAb E26. DPPIV activity from cell lysates HS578T (panels A and B) or LOX (panels C and D) measured after antibody binding: with E19 (panels A and C) or E26 (panels B and D). Control: (lightly shaded columns), the 96well plate was first coated with rabbit anti-rat IgG, washed 5× and then coated with the first mAb. Lysates were then bound. Direct inhibition: (black columns) the 96well plate was first coated with rabbit anti-rat IgG, washed 5× and then coated directly with E19 or E26. Lysates were then bound. Indirect inhibition (medium shaded columns) the 96well plate was first coated with rabbit anti-rat IgG, washed 5× and then coated with the anti-seprase/DPPIV mAb. Lysates were then bound. After washing, E19 or E26 was added and assayed for peptidase activity.

DETAILED DESCRIPTION OF THE INVENTION

Definitions

As used in this application, the following words or phrases have the meanings specified.

As used herein, "fragment" is defined as at least a portion of the variable region of the immunoglobulin molecule which binds to its target, i.e. the antigen binding region. Some of the constant region of the immunoglobulin may be included.

As used herein, an "immunoconjugate" means any molecule or ligand such as an antibody or growth factor chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as it is able to bind its target. Examples of immunoconjugates include immunotoxins and antibody conjugates.

As used herein, "selectively killing" means killing those cells to which the antibody binds.

As used herein, examples of "carcinomas" include bladder, breast, colon, liver, lung, ovarian, and pancreatic carcinomas.

As used herein, "immunotoxin" means an antibody or growth factor chemically or biologically linked to a cytotoxin or cytotoxic agent.

As used herein, an "effective amount" is an amount of the antibody, immunoconjugate, recombinant molecule which kills cells or inhibits the proliferation thereof.

As used herein, "competitively inhibits" means being capable of binding to the same target as another molecule. With regard to an antibody, competitively inhibits mean that the antibody is capable of recognizing and binding the same antigen binding region to which another antibody is directed.

As used herein, "antigen-binding region" means that part of the antibody, recombinant molecule, the fusion protein, or the immunoconjugate of the invention which recognizes the target or portions thereof.

As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radio-isotope which is effective in destroying a tumor. Examples include, but are not limited to, cobalt-60 and X-rays. Additionally, naturally occurring radioactive elements such as uranium, radium, and thorium which typically represent mixtures of radioisotopes, are suitable examples of a radioactive agent.

As used herein, "administering" means oral administration, administration as a suppository, topical contact, intravenous, intraperitoneal, intramuscular or subcutaneous administration, or the implantation of a slow-release device such as a miniosmotic pump, to the subject.

As used herein, "curing" means to provide substantially complete tumor regression so that the tumor is not palpable.

As used herein, "tumor associated antigens" means any cell surface antigen which is generally associated with tumor cells, i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "pharmaceutically acceptable carrier" includes any material which when combined with the antibody retains the antibody's immunogenicity and non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods

DESCRIPTION OF THE INVENTION

The invention provides monospecific antibodies which specifically bind an epitope of a human DPPIV (dipeptidyl peptidase IV/CD26) and inhibits angiogenesis. The monospecific antibodies of the present invention include monoclonal, chimeric and humanized antibodies and antibody fragments that specifically bind the epitopes bound by either of the anti-DPPIV antibodies E19 or E26. In a preferred embodiment the antibody fragments comprise the antigen-binding region of the antibody.

In one embodiment the monospecific antibodies of the present invention include those that bind specifically with the catalytic or substrate-binding domains of human DPPIV (dipeptidyl peptidase IV also known as CD26).

In another embodiment the antibodies of the present invention specifically bind invadopodia of cells of a tissue undergoing angiogenesis. Such cells may be cancerous cells, cells of a tumor in a human being in vivo, or the cells may be cells may comprise a tissue or an organ undergoing an ex-vivo procedure.

The antibodies or antibody fragments of the present invention exhibit one or more of the following characteristics:

i) the antibodies specifically bind to the invadopodia of invasive cells grown in collagen or on fibronectin films ii) the antibodies antibody fragments fail to react with non-invasive human carcinoma cells grown in collagen or on fibronectin films.

iii) the antibodies antibody fragments bind weakly to differentiated human endothelial cells in collagen or matrix gels and more strongly to sprouting human endothelial cells in collagen or matrix gels, iv) the antibodies antibody fragments bind weakly with connective tissue cells and more strongly with these induced by wounding, and v) the antibodies antibody fragments block the interaction of collagen matrix with reactive human cells and inhibit the collagen degradation by such cells.

vi) the antibodies or antibody fragments react readily with the catalytic or substrate-binding domains of DPPIV and of the seprase-DPPIV complex.

The antibodies of the present invention may comprise a seprase-DPPIV antagonist for use in the present methods. Such seprase-DPPIV antagonists are capable of binding to the catalytic and substrate-binding domains and competitively inhibiting the ability of seprase-DPPIV to interact with a natural ligand such as type I or IV collagen. Preferably, the antagonist exhibits specificity for seprase and DPPIV over other proteases, including urokinase and matrix metalloproteases. In a particularly preferred embodiment, a polypeptide or antibody fragment react readily with the catalytic or substrate-binding domains of the seprase-DPPIV complex and inhibits binding of collagen or E19 and E26 monoclonal antibodies to said domains. A preferred seprase-DPPIV antagonist may be a polypeptide or a monoclonal antibody, or functional fragment thereof, that is immunoreactive with either the catalytic or substrate-binding domains (or both) of the seprase-DPPIV complex. In one embodiment the antibody competitively inhibits the peptidase activity of DPPIV.

Also provided by the present invention are bispecific antibodies with binding specificity for two epitopes, one of which is an epitope of DPPIV. The bispecific antibodies of the present invention include those in which the second epitope bound is an epitope of seprase, MT1-MMP, MMP-2 or an integrin, such as α(3)β(1)-integrin, αvβ3 integrin or β1 integrin. The second epitope may be an epitope of any tumor-associated antigen.

The present invention further provides immunoconjugates comprising a monospecific antibody which specifically binds an epitope of human DPPIV (dipeptidyl peptidase IV/CD26) and inhibits angiogenesis, joined to a therapeutic agent. These immunoconjugates include those which comprises the monoclonal antibodies E19 or E26 or fragments of such antibodies. In a preferred embodiment the immunoconjugate is capable of killing cells involved in angiogenesis.

Alternatively the immunoconjugates of the present invention may include recombinant, chimeric, or humanized antibodies; or fragments of any of these. The immunoconjugates of the present invention may comprise a therapeutic agent such as an anti-tumor drug, a cytotoxin, a radioactive agent, a photosensitizer, a second antibody or an enzyme.

In yet another aspect the invention provides pharmaceutical compositions for inhibiting angiogenesis comprising an effective amount of a monospecific antibody which specifically binds an epitope of a human DPPIV (dipeptidyl peptidase IV/CD26) and inhibits angiogenesis, the antibody being formulated in a pharmaceutically acceptable carrier.

The invention further provides pharmaceutical compositions for inhibiting angiogenesis comprising an effective amount of a bispecific antibody which specifically binds an epitope of a human DPPIV (dipeptidyl peptidase IV/CD26) and inhibits angiogenesis, the antibody being formulated in a pharmaceutically acceptable carrier.

In yet another aspect the invention provides pharmaceutical compositions for inhibiting angiogenesis comprising an effective amount of an immunoconjugate of a monospecific or a bispecific antibody which specifically binds an epitope of a human DPPIV (dipeptidyl peptidase IV/CD26) and inhibits angiogenesis, the antibody being formulated in a pharmaceutically acceptable carrier.

The present invention yet further provides a method of treating a patient suffering from a growth or proliferative disorder involving angiogenesis, comprising administering an effective amount of a monospecific antibody which specifically binds an epitope of a human DPPIV (dipeptidyl peptidase IV/CD26) and inhibits angiogenesis.

The present invention also provides a method of treating a patient suffering from a growth or proliferative disorder involving angiogenesis, comprising an effective amount of a bispecific antibody which specifically binds an epitope of a human DPPIV (dipeptidyl peptidase IV/CD26) and inhibits angiogenesis.

In yet another aspect the present invention provides a method of treating a patient suffering from a growth or proliferative disorder involving angiogenesis, comprising administering an effective amount of an immunoconjugate of a monospecific antibody which specifically binds an epitope of a human DPPIV (dipeptidyl peptidase IV/CD26) and inhibits angiogenesis.

The present invention further provides a method of treating a patient suffering from a growth or proliferative disorder involving angiogenesis, comprising administering an effective amount of an immunoconjugate of a bispecific antibody which specifically binds an epitope of a human DPPIV (dipeptidyl peptidase IV/CD26) and inhibits angiogenesis.

The anti-angiogenic treatment methods of the invention described above may be applied to patients with solid tumors, preferably to inhibit angiogenesis and metastasis, and most preferably to induce tumor regression. More preferably still, the treatment methods are capable of curing the patient of the tumor such that tumor regression is substantially complete.

Also provided are continuing hybridoma cell lines, which secrete recoverable quantities of monoclonal antibodies which specifically bind an epitope of a human DPPIV (dipeptidyl peptidase IV/CD26) and inhibits angiogenesis. In a particular embodiment the hybridoma is one that produces a monoclonal antibody of the class IgG.sub. 2a, designated E19. In another particular embodiment the hybridoma is one that produces a monoclonal antibody of the class IgG.sub. 2a, designated E26.

The invention relates to a membrane protease complex, consisting of two homodimers of seprase and dipeptidyl peptidase IV (DPPIV), initially obtained from human placental capillary endothelial membranes, monoclonal antibodies against the same and a method of inhibiting capillary sprouting and angiogenesis in human cancer.

Two novel rat monoclonal antibodies of the class IgG.sub.2a react readily with the protease complex consisting of seprase and DPPIV that resides on cell surface invadopodia at the leading edge of angiogenic endothelia, migratory fibroblasts, and invading cancer cells. These antibodies fail to react with resting cells in adjacent human tissues and blood vessels. They also block interaction of collagen matrix with the seprase-DPPIV complex in the invasive cells during angiogenesis and cancer spreading but not that with other endothelia or tumor cells not undergoing angiogenesis.

The disclosures of the present invention herein demonstrates that angiogenesis in tissues requires a membrane protease complex, consisting of two homodimers of seprase and dipeptidyl peptidase IV (DPPIV), and that inhibitors of the seprase-DPPIV complex can inhibit angiogenesis. The disclosure also demonstrates that antagonists of two novel rat monoclonal antibodies of the class IgG.sub.2a react readily with the catalytic and substrate-binding domains of the protease complex that resides on cell surface invadopodia at the leading edge of angiogenic endothelia, migratory fibroblasts, and invading cancer cells, while failing to react with resting cells in adjacent human tissues and blood vessels. These antibodies have the property of blocking interaction of collagen matrix with the seprase-DPPIV complex in the invasive cells during angiogenesis and cancer spreading but not that with other endothelia or tumor cells.

The invention describes methods for inhibiting angiogenesis and cancer metastasis in a tissue comprising administering to the tissue a composition comprising an effective amount of a seprase-DPPIV antagonist such as monoclonal antibody E19 or monoclonal antibody E26.

The tissue to be treated can be any tissue in which inhibition of angiogenesis or cell invasion is desirable, such as diseased tissue where neo-vascularization or cancer spreading is occurring. Exemplary human tissues include various types of carcinoma, metastases, tissues undergoing restenosis, inflamed tissue, and the like tissues.

A seprase-DPPIV antagonist for use in the present methods is capable of binding to the catalytic and substrate-binding domains and competitively inhibiting the ability of seprase-DPPIV to interact with a natural ligand such as type I or IV collagen. Preferably, the antagonist exhibits specificity for seprase and DPPIV over other proteases, including urokinase and matrix metalloproteases. In a particularly preferred embodiment, a polypeptide or antibody fragment react readily with the catalytic or substrate-binding domains of the seprase-DPPIV complex and inhibits binding of collagen or E19 and E26 monoclonal antibodies to said domains. A preferred seprase-DPPIV antagonist can be a polypeptide or a monoclonal antibody, or functional fragment thereof, that immunoreacts with the catalytic or substrate-binding domains of the seprase-DPPIV complex.

Seprase and DPPIV are activated on specialized protrusions (invadopodia) of migratory endothelial cells. Both seprase and DPPIV are transiently expressed in endothelial cells at sites of sprouting vessels but not in differentiated vessels in human breast cancer tissue or in human angiogenesis models. In contrast, other known targets for anti-angiogenesis therapies which include β1 integrins, MT1-MMP and MMP-2 are constitutively expressed in endothelial cells. Antibodies to DPPIV blocked endothelial migration and sprouting but did not affect preexisting capillaries; whereas β1 integrin antibodies or MMP inhibitors strongly disturbed both processes. Because seprase and DPPIV are co-expressed at very low levels in differentiated endothelium, they make attractive new therapeutic targets for cancer angiogenesis.

EXAMPLES

Methods

Following methods were carried out as described: immunohistological staining of tissue sections (Kelly et al., 1998); seprase/DPPIV protein and proteolytic activity (Pineiro-Sanchez et al., 1997); RT-PCR (Goldstein et al., 1997); double-labeled immunofluorescence of cultured cells and β1 integrin blotting (Mueller et al., 1999), MMP-2 activity (Nakahara et al., 1997); endothelial migration and monolayer wound assays (Pepper et al., 1996); HUVEC culture and Matrigel tube assay (Grant et al., 1992).

Example 1
Cytoimmunohistochemical Staining for Seprase and DPPIV in Endothelial Cells Sprouting Vessels and in Normal Tissue To investigate the expression of seprase and DPPIV during angiogenesis, human malignant breast carcinoma tissue or adjacent normal skin were stained with antibodies specific for either seprase or DPPIV. Both seprase and DPPIV were abundantly expressed on the endothelial cells of sprouting vessels (FIG. 1, solid arrows) but were not detectable in other tumor vessels (FIG. 1, open arrows) or in adjacent normal skin from the same donor. These findings indicate that only sprouting sites of blood vessels involved in tumor angiogenesis have enhanced expression of seprase and DPPIV. Consistent with this result, expression of seprase and DPPIV on cultured endothelial cells can be induced by means or factors that enhance cell migration and vessel sprouting (see below).

Figure 2A:
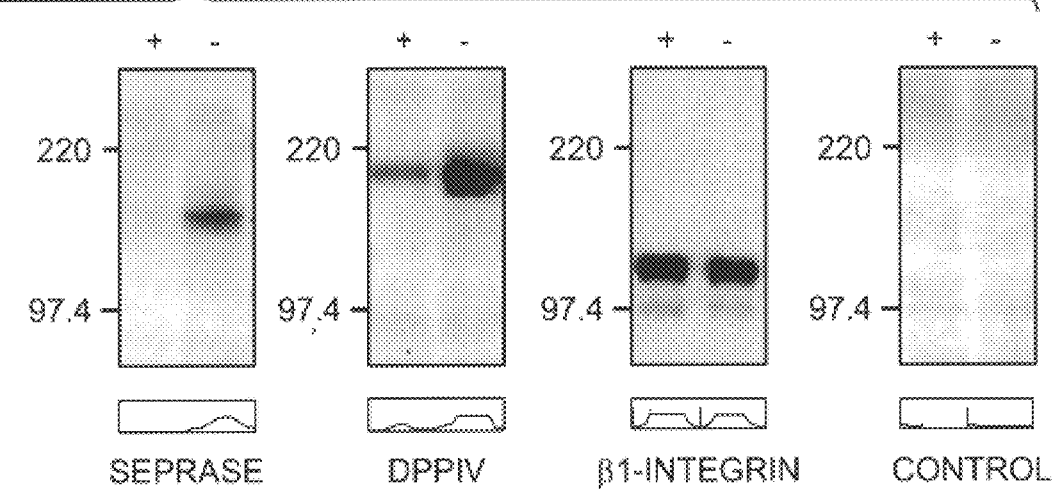
FIGS. 2A–J. Enhanced expression and proteolytic activities of seprase and DPPIV in migratory endothelial cells. a–e, Seprase/DPPIV expression, proteolytic activities and mRNA profiles were analyzed in confluent (+) and sparse (–) HUVEC. a, Immunoblotting analysis of cell lysates using anti-seprase (D28, Piniero-Sanchez et al., 1997), DPPIV (E26), β1 integrin (C27, Bloch et al., 19977) and antibody control. The immunoblots and their densitometry scans (adjoining panels) show that both seprase and DPPIV are elevated in sparse cultures, while β1 integrin remains the same in confluent (+) and sparse (–) conditions. b, Gelatin zymography of cell lysates in the presence of Ca++ (+2 mM $CaCl_2$) and deprived of Ca++ (+2 mM EDTA). The 170-kDa gelatinase (seprase) activity was elevated in sparse cultures, while the 62-kDa MMP-2 activity remained the same in confluent (+) and sparse (–) conditions. c, DPPIV substrate Gly-Pro-AFC (7-Amino-4-Trifluoromethyl Couramin) overlay of cell lysates. The 200-kDa DPPIV activity was increased in the sparse culture. d, Detection of seprase RNA. RT-PCR was carried out on total RNA from LOX human malignant melanoma cells (Lox)—a positive control (Goldstein et al., 1997) and confluent (+) and sparse (–) HUVEC using oligonucleotide primers "FAP1+2" and "FAP11+4" that correspond to specific nucleotide positions of the seprase cDNA as described (Goldstein et al., 1997).
Figure 2B:
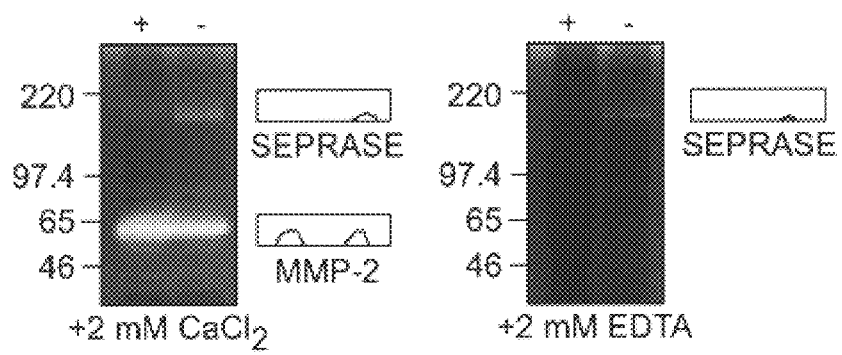
Figure 2C:
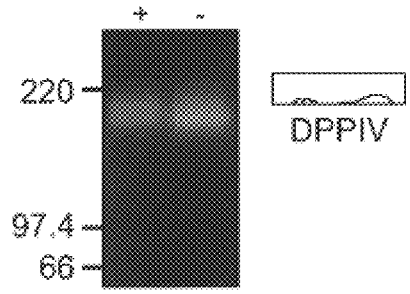

Example 2
Cytoimmunohistochemical Staining for Seprase and DPPIV in Human Primary Cell Culture Monolayers of Different Cell Densities Endothelial cells of sprouting vessels are migratory and exhibit a lack contact inhibition (Pepper et al., 1993). Monolayer cultures of human umbilical vein endothelial cells (HUVEC) can be induced to migrate by wounding or passage to low cell density (Pepper et al., 1996). This assay was used to examine the expression of seprase and DPPIV in migratory endothelial cells. The confluent HUVEC monolayers were found to contain low levels of seprase and DPPIV and their proteolytic activities were also low (FIGS. 2a–c). Passage of monolayers into a sparse culture within 24 hours induced the expression of functional seprase protein; it also caused an increase in DPPIV protein and their proteolytic activities (FIGS. 2a–c).

Figure 2D:
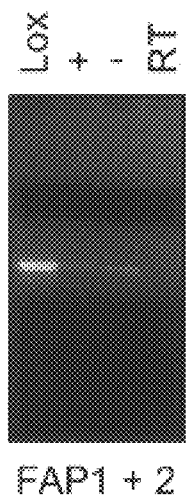
Figure 2D:
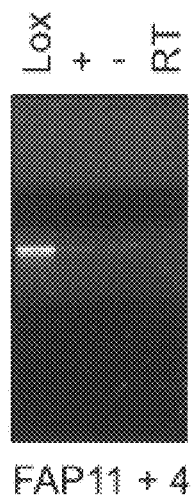
Figure 2D:
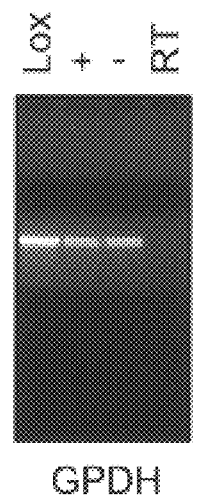
Figure 2E:
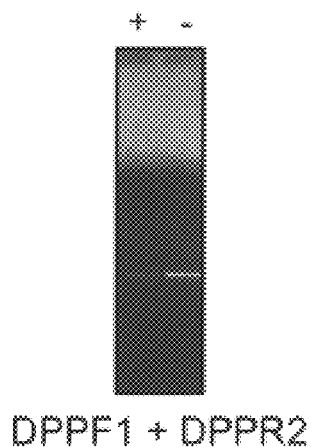

Both HUVEC cultures had detectable seprase and DPPIV mRNA (FIGS. 2d–e). As β1 integrins (Bloch et al., 1997) and membrane-bound MMP-2 (Hiraoka et al., 1998) have been shown to be essential for angiogenesis, we examined their presence in this assay. β1 Integrin and MMP-2 gelatinase activity were readily detectable in both confluent and sparse endothelial cultures, while seprase and DPPIV (protein/activity) were increased in the sparse culture (FIGS. 2a–b). The result strongly suggests the association of seprase and DPPIV expression with migratory activity of endothelial cells.

Figure 2F:
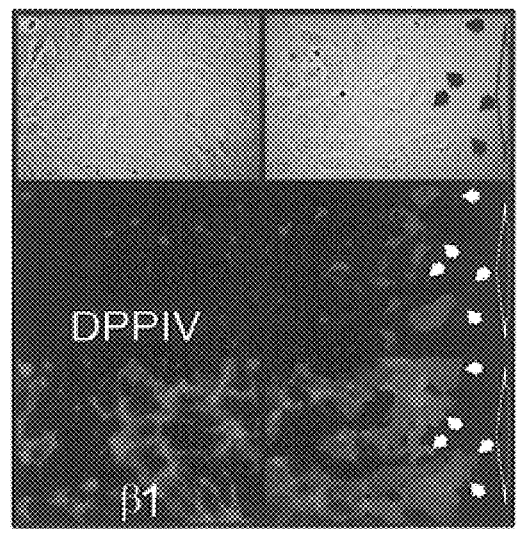
Figure 2G:
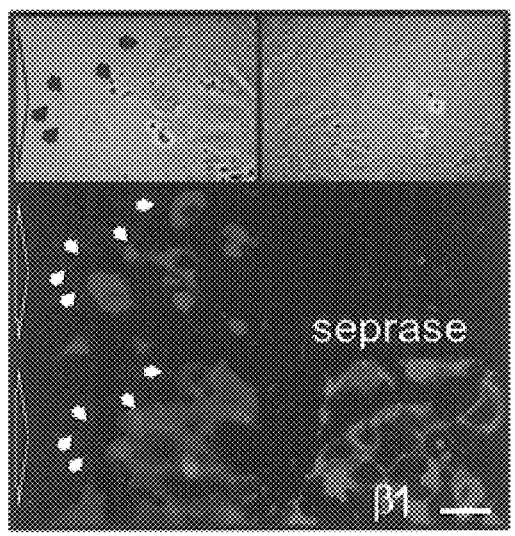

Example 3
Expression of Seprase/DPPIV and β1 Integrins During Wound-induced Endothelial Migration The relative expression of seprase/DPPIV and β1 integrins during wound-induced endothelial migration was examined by double-labeled immunofluorescence. The monolayer wound model consists of a 300 μm width wound on the HUVEC monolayer; migratory activity of HUVEC was visible one hour after wounding (FIGS. 2f–g). Expression of β1 integrins was high in endothelial cells at both the wound edge (wounded) and in the monolayer (stationary); in contrast, seprase and DPPIV expression was restricted to migratory cells at the wound edge (FIGS. 2f–g, arrows).

In addition, seprase and DPPIV expression was found on invadopodia (FIGS. 2f–g, arrows) and on the perinuclear region (Golgi apparatus) of migratory cells but not in confluent cells. In phase contrast images (FIGS. 2f–g), β1 integrins were distributed widely on the surface of migratory cells (FIGS. 2f–g, solid arrows) and particularly concentrated at sites of contact between confluent cells, suggesting the role of integrins in both cell migration and adhesion. Similar to β1, membrane type-1 MMP was found distributed evenly on the cell surface of HUVEC at the wound edge and in stationary monolayers.

Figure 2H:
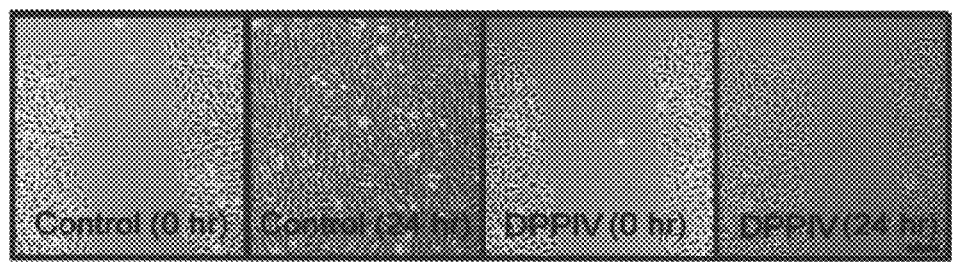
Figure 2I:
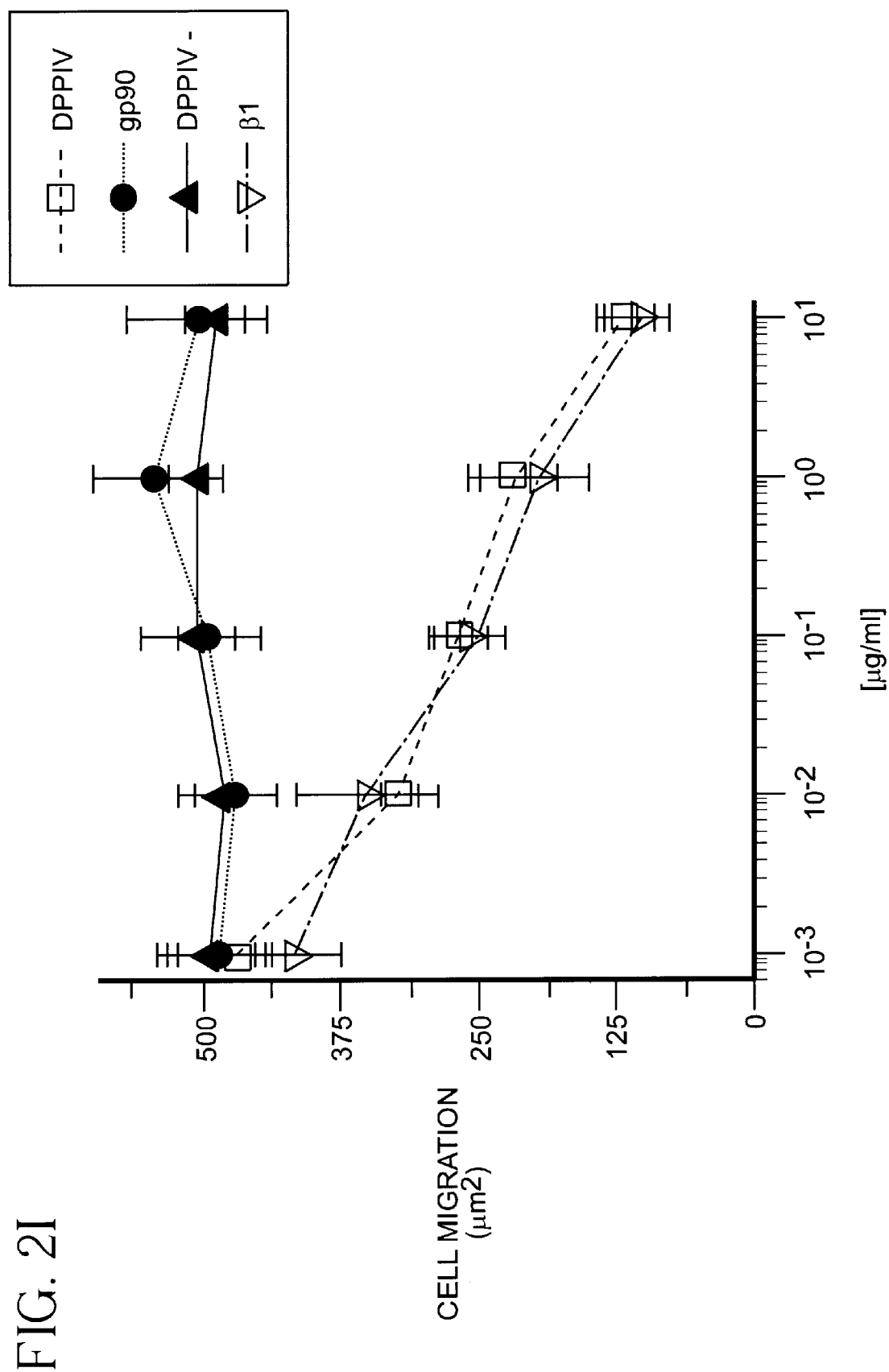
Figure 2J:
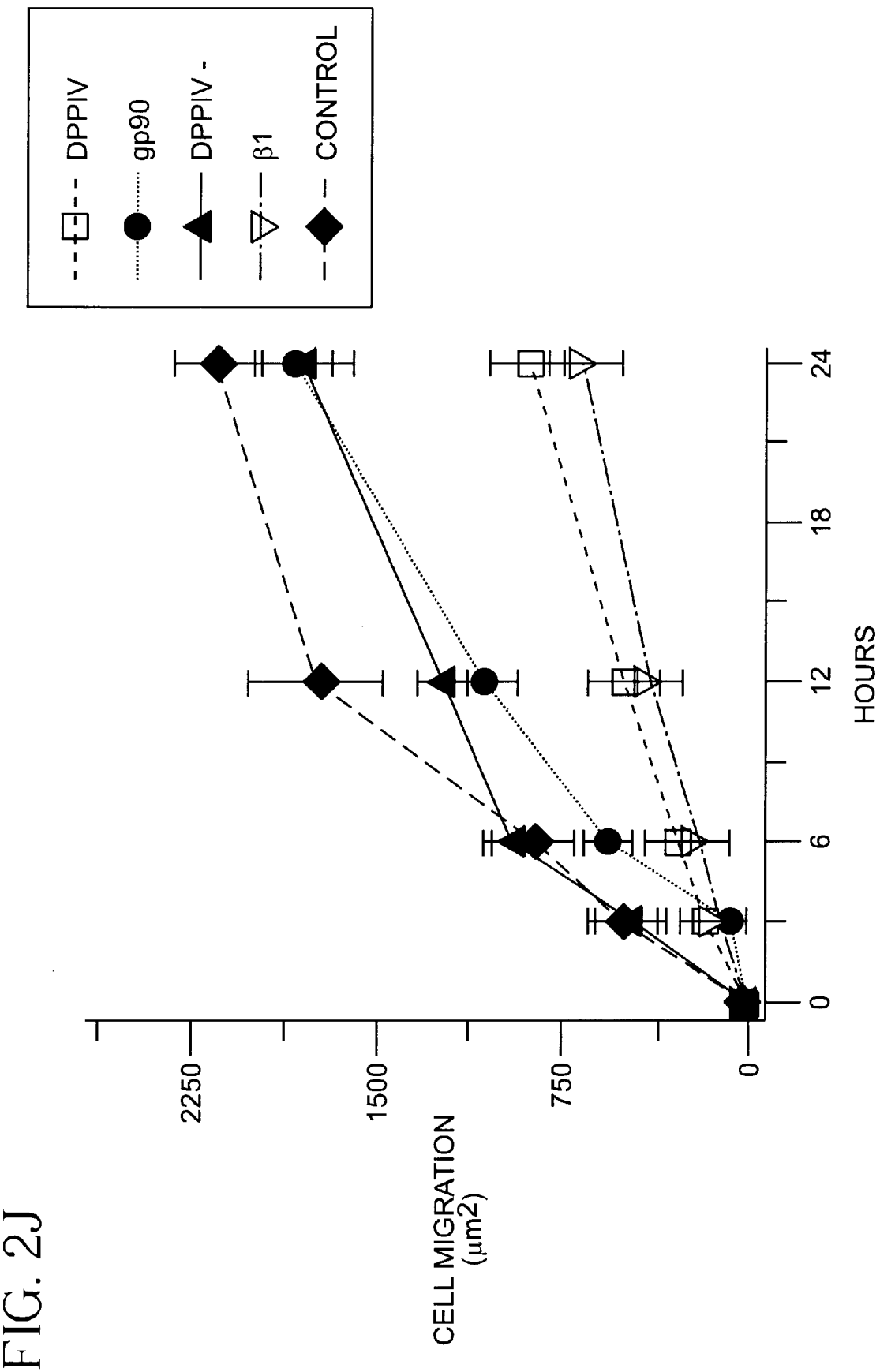

Example 4
Inhibitory Effects of Anti-DPPIV mAbs on Cell Migration of Fibroblasts and of Wounded Cells from a Monolayer The effect of various mAbs against DPPIV (E19 and E26 are inhibitory; E3 is not), β1 integrins (C27 and 13 are inhibitory), and a cell surface glycoprotein gp90 (C37 is not inhibitory) (Mueller et al., 1999) were examined to determine whether DPPIV (and possibly seprase) plays an active role in endothelial migration. Both anti-DPPIV and anti-β1 mAbs blocked endothelial cell migration, whereas the mAb against cell surface proteins gp90 had no effect (FIGS. 2h–j). Identical results were obtained when fibroblast migration and cell surface collagen degradation were induced by monolayer wounding.

Figure 3A:
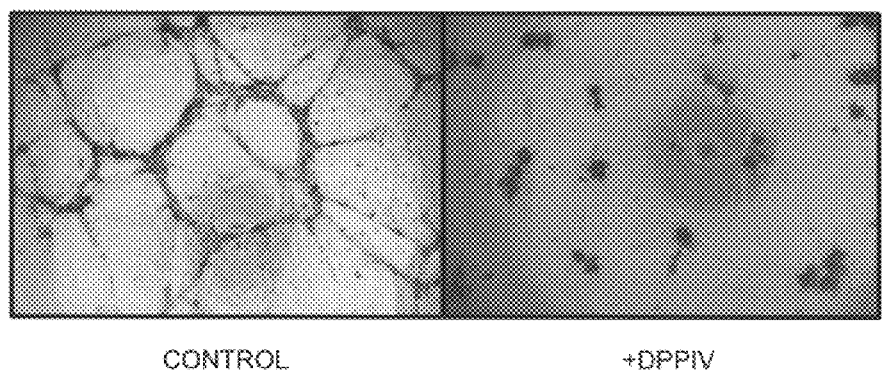
Figure 3B:
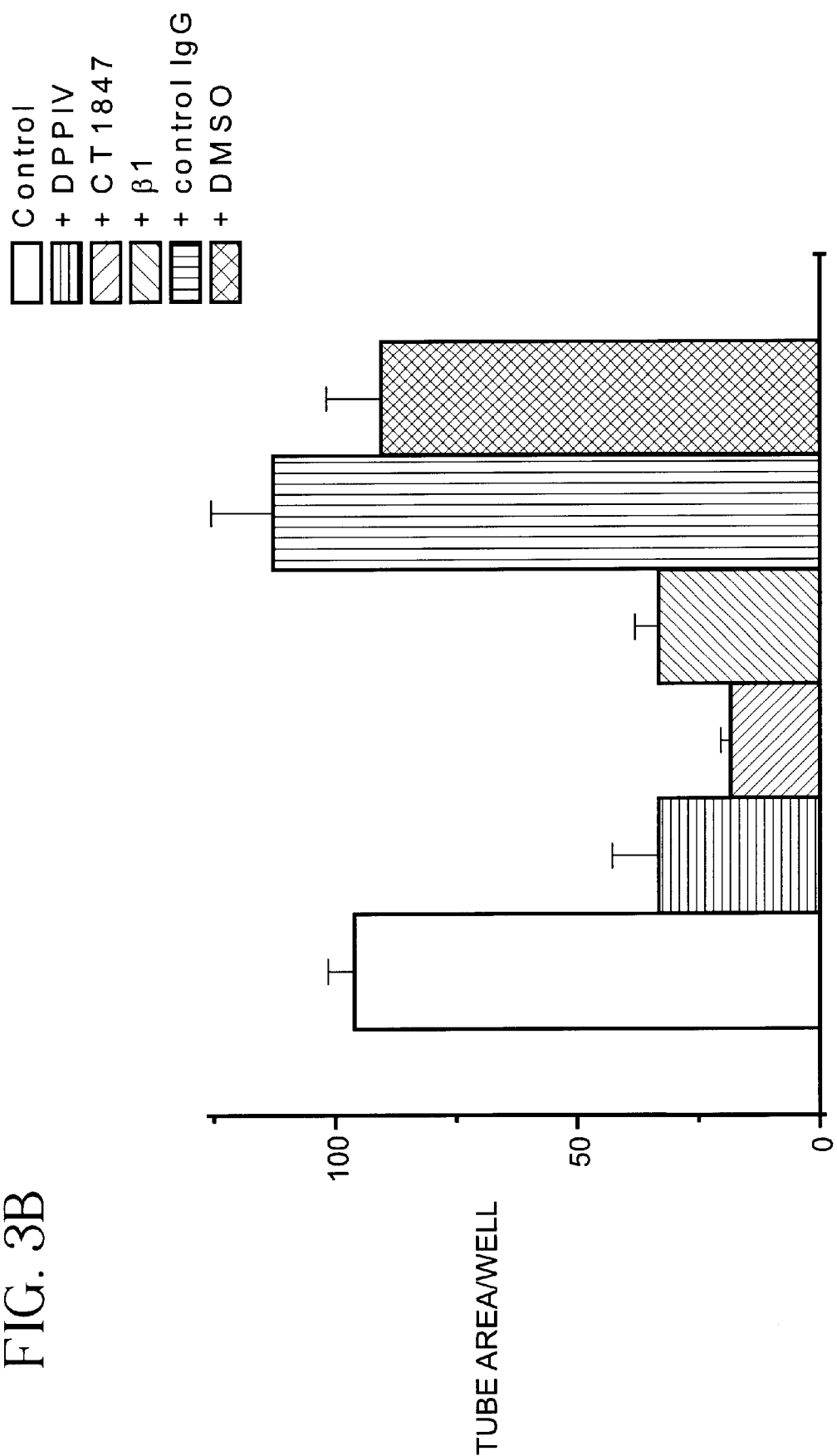

Example 5
Inhibitory Effects of Anti-DPPIV mAbs on Blood Vessel Tube Formation To examine the effects of these same antibodies on endothelial tube formation by Matrigel (Grant et al., 1992), mAbs or the matrix metalloprotease inhibitor CT1847 (Zucker et al., 1998) were added prior to or after tube formation (FIG. 3a). The inhibitory anti-DPPIV and β1 mAbs and CT1847 blocked tube formation in Matrigel (FIG.

Figure 3C:
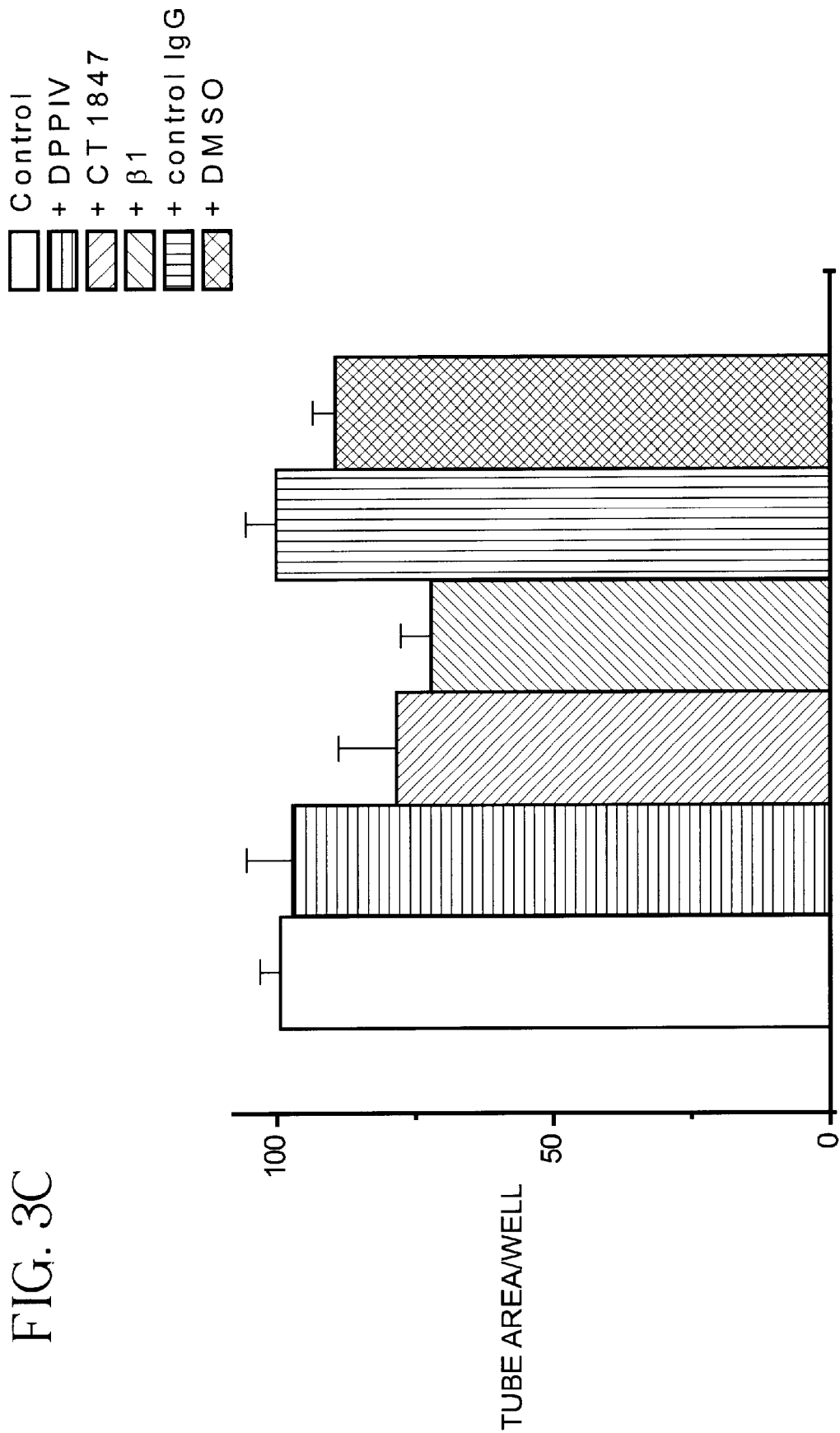
Figure 3D:
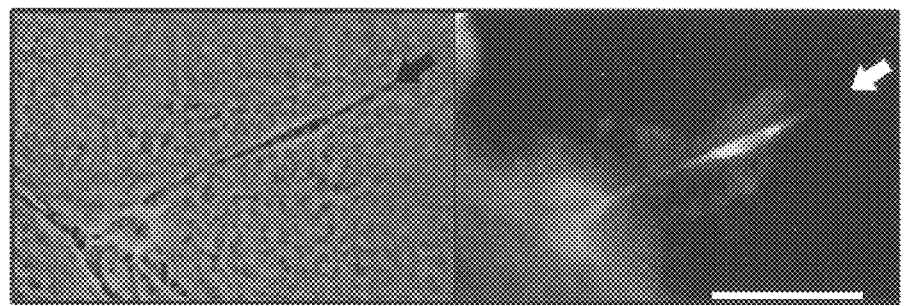

3b); however, only anti-β1 mAb and CT1847 but not the anti-DPPIV mAb perturbed preexisting tubes (FIG. 3c). None of the other mAbs to DPPIV and seprase affected preexisting endothelial tubes. Specific expression of seprase and DPPIV in the endothelial cell migrated from a forming tube (FIG. 3d) also supports the observation that the anti-DPPIV mAb appears to act selectively on new tube formation.

Example 6

Effects of Anti-DPPIV mAbs on Invasion and Capillary Sprout Formation of Human Dermal Microvascular Endothelial Cells (HDMEC)

In a recently developed in vitro human angiogenesis model, invasion and capillary sprout formation of HDMEC can be induced in fibrin gels in response to vascular endothelial growth factor (VEGF) and basic fibroblast growth factor (bFGF). This assay was used to determine whether DPPIV plays an active role in human angiogenesis. HDMEC were cultured on microcarrier beads and embedded in a three dimensional human fibrin gel that contained VEGF and bFGF. In this model, HDMEC formed capillary sprouts [within 24 hours] (FIG. 4a, upper pictures labeled with VEGF/bFGF+ or −). The presence of a capillary lumen was confirmed by confocal microscopy. When the fibrin gel was impregnated with the inhibitory anti-DPPIV or β1 antibodies or CT1847, capillary sprouting was blocked (FIGS. 4a–b).

Example 7
The Active Domain of the Seprase-DPPIV Complex

Recent cloning studies (Goldstein et al., 1997) show that seprase carboxyl terminus contains a putative catalytic region (~200 amino acids), which is homologous (68% identity) to that of the non-classical serine peptidase DPPIV. The conserved serine protease motif G-X-S-X-G is present as G-W-S-Y-G. Like DPPIV, seprase have 12 Cys with 6 residues being conserved in the Cys rich region and 3 in the catalytic region. Seprase has a peculiar protease inhibitor profile: it is inhibited by the protease inhibitors, including PMSF and NEM (Aoyama and Chen, 1990). Its gelatinase activity was completely blocked by the serine-protease inhibitors, DFP, PMSF, AEBSF, and APSF. Dimeric seprase could be affinity-labeled by [$^3$H]-DFP but the proteolytically inactive 97-kDa subunit could not (Pineiro-Sanchez et al., 1997). The inhibitor and substrate specificity of the seprase-DPPIV complex isolated from human breast carcinoma cells was analyzed by [$^3$H]-DFP labeling. The method is extremely sensitive to detect serine proteases and esterases ($10^{-13}$ M) and is based upon the stoichiometrical, covalent binding of [$^3$H]-DFP into the proteases that are reduced in the presence of their substrates and inhibitors. Both dimeric seprase and DPPIV may be labeled with [$^3$H]-DFP and their molecular identity may be visualized on SDS gels (Pineiro-Sanchez et al., 1997). By incubating the seprase-DPPIV complex with [$^3$H]-DFP in the presence of their peptide-substrates or inhibitors, the protease inhibition is quantified.

Seprase and the seprase-DPPIV complex were purified from $10^{11}$ LOX human malignant melanoma cells or MDA-MB-436 human breast carcinoma cells that express seprase and the seprase-DPPIV complex, respectively. Cell lysates are subjected to two steps of enrichment (Triton X-114 detergent phase partitioning and WGA chromatography) and they are stored at −80° C. Purified seprase is prepared immediately prior to experimentation by immunoprecipitation of LOX WGA-binding proteins with micro-magnetic beads (about 50 nm, Miltenyi Biotec) using mAb D28 or D8. The seprase-DPPIV complex is purified from MDA-MB-436 WGA proteins with either anti-seprase- or anti-DPPIV-monoclonal antibodies. Purified seprase and the seprase-DPPIV complexes are used to define inhibitor- and substrate-specificity of the enzymes.

Example 8
Substrate Specificity of the Seprase-DPPIV Complex that was Purified by Monoclonal Antibodies Collagen-substrate specificity of the seprase-DPPIV complex was determined by incubating fluorescently labeled type I collagen with isolated seprase, DPPIV or seprase-DPPIV complex in the presence of SIMP inhibitors (PMSF inhibits seprase activity and it can be used as control). Briefly, fluorescently labeled collagen was incubated with seprase, DPPIV or seprase-DPPIV complex immobilized on mAb-beads at 37° C., in the presence or absence of enzyme inhibitors. The cleavage site of type I collagen by isolated seprase, DPPIV or seprase-DPPIV was examined. Rates of cleavage and fragment sizes was analyzed by SDS-PAGE as shown in a previous paper (Pineiro-Sanchez et al., 1997). Cleavage products, transferred to an Immobilon-P membrane was subjected to limited sequence analysis to determine the primary cleavage site(s) (Pineiro-Sanchez et al., 1997). The seprase-cleavage peptides include proline and hydroxyproline.

Example 9
X-Proline Dipeptide Bonds as Cleavage Sites of Seprase and Seprase-DPPIV Complex Amino acid cleavage site of individual seprase or the seprase-DPPIV complex were identified to be at X-proline dipeptide bond using method described in a previous paper (Pineiro-Sanchez et al., 1997). Classical DPPIV activity using the fluorescent Ala-Pro-AFC substrate overlay assay showed that SDS-denatured seprase or the protease complex exhibited little activity. However, native seprase and the protease complex purified by monoclonal antibodies from LOX or MDA-MB-436 or Hs578T tumor cells show strong activity toward glycine-proline or alanine-proline etc (X-proline) dipeptide bonds. See FIGS. 5 and 6 and the descriptions of the figures for details. In addition, the figures show that mAbs E19 and E26 interfered with the glycine-proline cleavage by LOX- or Hs578T-seprase complex purified by monoclonal antibodies.

Seprase degrades denatured collagens that contain high levels of proline peptides. Its catalytic domain sequence is highly homologous to that of the proline-specific exopeptidase DPPIV. Seprase and the seprase-DPPIV complex cleaves proline-peptide bonds including for example the following:

(omega-N-(O-acyl)hydroxy amid) aminodicarboxylic acid pyrrolidides (Demuth et al., 1993) and substrates containing phosphorylated residues adjacent to proline (Kaspari et al., 1996), which are potent inhibitors of proline-specific peptidases.
H-Ile-Pro-NHO-pNB, irreversible suicide DPPIV inhibitor
H-Ile-Thia, reversible DPPIV inhibitor (Ki=8*10-8)
H-Glu(NHO-Bz)-Pyrr, reversible DPPIV inhibitor (Ki= 5*10-7)
H-Glu(Gly5)-Thia, reversible DPPIV inhibitor (Ki=8*10-8)
H-Pro-Ile-Thia, reversible PEP inhibitor
pGlu-Ile-Thia, reversible PEP inhibitor
Boc-Ile-Pyrr, reversible PEP inhibitor
Boc-Glu(NHO-Bz)-Pyrr, reversible, slowly acylating PEP inhibitor
Z-Phe-Ala-CMK, irreversible PEP inhibitor
Z-Gly-Pro-AMC, fluorgenic PEP substrate
H-Gly-Pro-AMC, fluorogenic DPPIV substrate.

Thus, small or large molecules interfering the interaction of seprase or the protease complex with X-proline in collagen have inhibitory activity for the seprase-DPPIV complex.

Example 10
Phage Displayed Peptides that Recognize Specific Sites of the Seprase-DPPIV Complex that was Purified by Monoclonal Antibodies Small peptides that specifically recognize the active sites of the seprase-DPPIV complex are identified using libraries of phage display peptides originally designed by George Smith (Scott and Smith, 1990). Using seprase or the seprase-DPPIV complex purified by mAbs E19 and D8, tens of billions of short peptides for tight binding to specific proteases are selected. The library is a vast mixture of filamentous phage clones, each displaying one-peptide sequence on the virion surface. The selection is accomplished by using the above protease preparations to affinity-purify phages that display tight-binding peptides and propagating the purified phage in E. coli. The amino acid sequences of the peptides displayed on the phage are then determined by sequencing the corresponding coding region in the viral DNAs. Specific peptides, displayed on filamentous phages that (i) bind to isolated enzyme or proteins, (ii) block enzymatic activity, and (iii) bind to inhibitory antibodies E19 and E26 against DPPIV are selected.

Such peptides that are recognized by monoclonal antibodies E19 or E26 may lead to the identification of a novel epitope involved in activity of the protease complex. For panning on monoclonal antibodies in (iii) above, inhibitory protease complex mAbs E19 and E26 are used to screen peptides from a random peptide library of 15 amino-acid residues as the approach previously used in the identification of human hepatitis B virus surface epitopes (Motti et al., 1994). The peptides that are recognized by the mAbs are analyzed for their amino acid similarity with the natural protease antigens, and the selected phage-displayed epitopes behave as antigenic mimics.

Example 11
Identification of Substrates for the Seprase-DPPIV Complex Using Bacteriophage Peptide Display Libraries and Monoclonal Antibody Purification of the Protease Complex Potential peptide substrates for seprase or the seprase-DPPIV complex are also identified using bacteriophage peptide display libraries that have been used by Navre's group to identify peptide substrates for stromelysin and matrilysin (Smith et al., 1995). The random hexamer library in the fd-derived vector fAFF-1 included a "tether" sequence that is recognized by monoclonal antibodies. The phage library is treated in solution with seprase or the seprase-DPPIV complex. Cleaved phage is separated from uncleaved phage using a mixture of tether-binding monoclonal antibodies and Protein A-bearing cells followed by precipitation. Clones are screened by the use of a rapid "dot-blot-proteolysis" assay as described in the above reference that identifies phage encoding peptide sequences susceptible to cleavage by the enzyme. The nucleotide sequence of the random hexamer region of isolated clones are determined. Synthetic peptides then are prepared whose sequences are based on some of the positive clones, as well as consensus sequences built from the positive clones. Seprase or specific seprase-DPPIV substrates that are both the most active and smallest are selected. The peptide substrates are used to conjugate with fluorescent AMC which in turn will be used in search for potential inhibitors using other phage peptide display libraries.

Example 12
General Procedure for Conjugating Small Molecular Drugs to an Antibody Antibody-small molecule conjugates are prepared by linking the DOX derivative maleimidocaproyl doxorubicin hydrazone or the maleimidocaproylhydrazone of Adriamycin to E19, E26 or control immunoglobulin following the procedure of Hellstrom, U.S. Pat. No. 5,980,896. Antibody is diluted with 0.0095 M PBS to a protein concentration of 10.49 mg/mL. This solution (500 mL) is heated to 37. degrees C., under a nitrogen atmosphere, in a water bath. Dithiothreitol (26.2 mL, 10 mM) in PBS is added and the solution is stirred for 3 hrs at 37. degrees C. The solution is divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mini-reservoir (Amicon, Division of W. R. Grace and Co., Beverly Mass. 01915-9843). Each reservoir contains 800 mL of 0.0095 M PBS-0.1 M L-histidine. The protein solutions are dialyzed until the concentration of free thiol in the filtrate was 63 .mu.M. The molar ratio of --SH/protein in the retentate is determined to be 8.16. The retentate is transferred from the cells to a sterile container under nitrogen and a solution of maleimidocaproyl hydrazone of adriamycin (42.6 mL, 5 mg/mL in water) is added with stirring. The conjugate is incubated at 4. degrees C. for 48 hrs after which it is filtered through a 0.22. mu. cellulose acetate membrane. A 2.5 cm.x0.50 cm Bio-Rad Econocolumn is packed with a slurry of 100 g of BioBeads.TM.SM-2 (Bio-Rad Laboratories, Richmond Calif. 94804) in 0.0095 M-0.1 M L-histidine buffer. The beads are prepared by washing in methanol, followed by water then several volumes of buffer. The filtered conjugate is percolated through this column at 2 mL/min. After chromatography the conjugate is filtered through a 0.22. mu. cellulose acetate membrane, frozen in liquid nitrogen and stored at −80. degrees. C. The conjugate obtained has a molar ratio of 6.77 Adriamycin to protein and is obtained in 80–95% yield.

Example 13
Biological Activity of Conjugates

Representative conjugates of the present invention are tested in both in vitro and in vivo systems to determine biological activity. In these tests, the potency of conjugates of cytotoxic drugs is determined by measuring the cytotoxicity of the conjugates against cells of human cancer origin. The following describes representative tests used and the results that are obtained. The conjugates are referred to using the form ligand-drug-molar ratio of ligand to drug.

Experimental Human Angiogenesis Assay

The assay system measures human angiogenesis, invasion and metastasis in the chimeric mouse:human model and is referred to as the experimental human angiogenesis assay. The assay has been described in detail by others, and further has been described herein to measure human angiogenesis, invasion and metastasis. See (Yan et al., 1993). Yan, et al., J. Clin. Invest., 91:986–996 (1993).

The experimental human angiogenesis assay is a useful assay model for in vivo angiogenesis because the transplanted skin grafts closely resemble normal human skin histologically. In this model, human cancer cell invasion and neovascularization are occurring wherein actual human blood vessels and tissue are growing from the grafted human skin into the human tumor tissue on the surface of the grafted human skin. The origin of the neovascularization into the human graft can be demonstrated by immunohistochemical staining of the neovasculature with human-specific endothelial cell markers. The invasion and metastasis of human cancer cells may be monitored also.

As demonstrated herein, the experimental human angiogenesis assay demonstrates regression of neovascularization based on both the amount and extent of regression of new vessel growth. Furthermore, effects on the invasion and metastasis of any cancer tissue transplanted upon the grafted skin are easily monitored. Finally, the assay is useful because there is an internal control for toxicity in the assay system. The SCID mouse is exposed to any test reagent, and therefore the health of the mouse is an indication of toxicity.

The experimental human angiogenesis model is prepared essentially as described in Yan, et al., J. Clin. Invest., 91:986–996 (1993). Briefly, a 2 cm.sup.2 square area of skin is surgically removed from a SCID mouse (6–8 weeks of age) and replaced with a human foreskin. The mouse is anesthetized and the hair removed from a 5 cm.sup.2 area on each side of the lateral abdominal region by shaving. Two circular graft beds of 2 cm.sup.2 are prepared by removing the fill thickness of skin down to the fascia. Full thickness human skin grafts of the same size derived from human neonatal foreskin are placed onto the wound beds and held in place with 5-0 monofilament suture (Dermalon, Davis and Geck Inc., Danbury, Conn.). The graft is covered with a Band-Aid, which is sutured to the skin. Micropore surgical tape (3M, St. Paul, Minn.) is also applied to cover the wound. Mice are housed in individual cages.

The LOX human melanoma cell line that expresses only seprase (Fodstad et al., 1988) or MDA-MB-436 breast carcinoma cell line that expresses the seprase-DPPIV complex (ATCC HTB 130), as determined by immunoreactivity of the cells with mAb D28 (anti-seprase) and E3 (anti-DPPIV), are used to form the solid human tumors on the human skin grafts on the SCID mice. A single cell suspension of 5.times.10 super.5 LOX or MDA-MB-436 cells is injected intradermally into the human skin graft. The mice are then observed for 2 to 4 weeks to allow growth of measurable human tumors.

Following the growth of measurable tumors, SCID mice, which had been injected with LOX or MDA-MB-436 human tumor cells, are injected intravenously into the tail vein with 250 .u.g of either the mAb E19/26 (anti-complex, inhibitory) or E3 (anti-DPPIV, non-inhibitory) twice a week for 2 to 3 weeks. After this time, the tumors are resected from the skin and trimmed free of surrounding tissue. Several mice are evaluated for each treatment with the average tumor weight from each treatment being calculated.

Exposure of the LOX- or MDA-MB-436-seprase complex positive human carcinoma tumor mass in the experimental human angiogenesis model to E19 or E26 (against the active site) causes the decrease from the non-inhibitory mAb E3 treated average tumor weight reduction of 100 mg. Representative examples of LOX tumors treated with the mAb E19 and E3 are examined morphologically. The E3-treated tumors remain large (8 to 10 mm in diameter) and well vascularized whereas those treated with mAb E19 (against the active site) are much smaller (3 to 4 mm in diameter) and lack detectable blood vessels. Thus, the blocking of the seprase-DPPIV complex by the intravenous application of active site-specific E19 or E26 antibodies results in a regression of a human melanoma or carcinoma in this model system.

Discussion

Recent studies demonstrated that proteases (MMPs (Hiraoka et al., 1998) and plasminogen activators (Pepper et al., 1993)) and integrins ($\alpha v\beta 3$ (Brooks et al., 1994) and $\beta 1$ (Bloch et al., 1997)) are implicated in angiogenesis. This report confirmed such observation that MMPs and $\beta 1$ integrins blocked all aspects of endothelial activities, including migration, sprouting and capillary stability. Particularly, our results demonstrate that the membrane-bound serine protease DPPIV and possibly seprase play a key role in endothelial migration and sprouting but not capillary stability. In addition, the findings that seprase/DPPIV are expressed specifically at sites of capillary sprouts, and that antibodies to DPPIV inhibited endothelial cell migration and capillary sprouting in various extracellular matrices, without perturbing preexisting capillaries, are consistent with the presumptive functioning of these proteases in angiogenesis.

Furthermore, DPPIV has been shown to be a gelatinase (Bermpohl et al., 1998) as well as an adhesion receptor for collagen (Bauvois, 1988; Hanski et al., 1988; Loster et al., 1995) or fibronectin (Cheng et al., 1998; Piazza et al., 1989; Johnson et al., 1993); whereas seprase, originally identified as a 170 kDa membrane-bound gelatinase, also associates with the adhesion receptor $\alpha 3\beta 1$ integrin (Aoyama and Chen, 1990; Mueller et al., 1999). Thus, seprase and DPPIV are specific targets for capillary sprouting.

The rat hybridoma that produces monoclonal antibody E26 was deposited with American Type Culture Collection, 10801 University Blvd., Manassas, Va. 20110 on May 15, 2001 under the terms of the Budapest Treaty and assigned patent deposit accession number PTA-3377. The rat hybridoma that produces monoclonal antibody E19 was deposited with American Type Culture Collection, 10801 University Blvd., Manassas, Va. 20110 on May 15, 2001 under the terms of the Budapest Treaty and assigned patent deposit accession number PTA-3378.

Those of skill in the art will immediately recognize further embodiments of the present invention which are exemplified in the specification and claims herein presented.

REFERENCES

Aoyama, A. and Chen, W.-T. (1990). A 170-kDa membrane-bound protease is associated with the expression of invasiveness by human malignant melanoma cells. Proc. Natl. Acad. Sci. U.S.A. 87, 8296–8300.

Bauvois, B. (1988). A collagen-binding glycoprotein on the surface of mouse fibroblasts is identified as dipeptidyl peptidase IV. Biochem. J. 252, 723–731.

Bermpohl, F., Löster, K., Reutter, W., and Baum, O. (1998). Rat dipeptidyl peptidase IV (DPP IV) exhibits endopeptidase activity with specificity for denatured fibrillar collagens. FEBS Letters 428, 152–156.

Bloch, W., Forsberg, E., Lentini, S., Brakebusch, C., Martin, K., Krell, H. W., Weidle, U. H., Addicks, K., and Fässler, R. (1997). b1 integrin is essential for teratoma growth and angiogenesis. J. Cell Biol. 139, 265–278.

Brooks, P. C., Clark, R. A., and Cheresh, D. A. (1994). Requirement of vascular integrin alpha v beta 3 for angiogenesis. Science 264, 569–571.

Brooks, P. C., Silletti, S., Von Schalscha, T. L., Friedlander, M., and Cheresh, D. A. (1998). Disruption of angiogenesis by PEX, a noncatalytic metalloproteinase fragment with integrin binding activity. Cell 92, 391–400.

Chen, W.-T. (1996). Proteases associated with invadapodia, and their role in degradation of extracellular matrix. Enzyme Protein 49, 59–71.

Chen, W.-T., Lee, C. C., Goldstein, L., Bernier, S., Liu, C. H., Lin, C. Y., Yeh, Y., Monsky, W. L., Kelly, T., Dai, M., and Mueller, S. C. (1994). Membrane proteases as potential diagnostic and therapeutic targets for breast malignancy. Breast Cancer Res. Treat. 31, 217–226.

Chen, W.-T. (1979). Induction of spreading during fibroblast movement. J. Cell Biol 81, 684–691.

Cheng, H. C., Abdel-Ghany, M., Elble, R. C., and Pauli, B. U. (1998). Lung endothelial dipeptidyl peptidase IV promotes adhesion and metastasis of rat breast cancer cells via tumor cell surface-associated fibronectin. J. Biol. Chem. 273, 24207–24215.

Folkman, J. (1995). Seminars in Medicine of the Beth Israel Hospital, Boston. Clinical applications of research on angiogenesis. N. England J. Med. 333, 1757–1763.

Folkman, J. (1990) J. Natl. Cancer Inst. 82:4–6.

Garin-Chesa, P., Old, L. J., and Rettig, W. J. (1990). Cell surface glycoprotein of reactive stromal fibroblasts as a potential antibody target in human epithelial cancers. Proc. Natl. Acad. Sci. USA 87, 7235–7239.

Goldstein, L. A., Ghersi, G., Pineiro-Sánchez, M. L., Salamone, M., Yeh, Y. Y., Flessate, D., and Chen, W.-T. (1997). Molecular cloning of seprase: A serine integral membrane protease from human melanoma. Biochim. Biophys. Acta Mol. Basis Dis. 1361, 11–19.

Grant, D. S., Kinsella, J. L., Fridman, R., Auerbach, R., Piasecki, B. A., Yamada, Y., Zain, M., and Kleinman, H. K. (1992). Interaction of endothelial cells with a laminin A chain peptide (SIKVAV) in vitro and induction of angiogenic behavior in vivo. J. Cell. Physiol. 153, 614–625.

Hanski, C., Huhle, T., Gossrau, R., and Reutter, W. (1988). Direct evidence for the binding of rat liver DPP IV to collagen in vitro. Exp. Cell Res. 178, 64–72.

Heins J, Welker P, Schonlein C, Born I, Hartrodt B, Neubert K, Tsuru D, Barth A 1988 Mechanism of proline-specific proteinases: (I) Substrate specificity of dipeptidyl peptidase IV from pig kidney and proline-specific endopeptidase from Flavobacterium meningosepticum. Biochim Biophys Acta 954(2):161–9.

Hiraoka, N., Allen, E., Apel, I. J., Gyetko, M. R., and Weiss, S. J. (1998). Matrix metalloproteinases regulate neovascularization by acting as pericellular fibrinolysins. Cell 95, 365–377.

Johnson, R. C., Zhu, D., Augustin-Voss, H. G., and Pauli, B. U. (1993). Lung endothelial dipeptidyl peptidase IV is an adhesion molecule for lung-metastatic rat breast and prostate carcinoma cells. J. Cell Biol 121, 1423–1432.

Kelly, T., Kechelava, S., Rozypal, T. L., West, K. W., and Korourian, S. (1998). Seprase, a membrane-bound protease, is overexpressed by invasive ductal carcinoma cells of human breast cancers. Mod. Pathol. 11, 855–863.

Klagsbrunn and Soker, (1993) Current Biology 3:699–702.

Loster, K., Zeilinger, K., Schuppan, D., and Reutter, W. (1995). The cysteine-rich region of dipeptidyl peptidase IV (CD 26) is the collagen-binding site. Biochem. Biophys. Res. Commun. 217, 341–348.

Morimoto, C. and Schlossman, S. F. (1994). CD26: A key costimulatory molecule on CD4 memory T cells. Immunologist 2, 4–7.

Martin, P. (1997). Wound healing—Aiming for perfect skin regeneration. Science 276, 75–81.

Monsky, W. L., Lin, C.-Y., Aoyama, A., Kelly, T., Mueller, S. C., Akiyama, S. K., and Chen, W.-T. (1994). A potential marker protease of invasiveness, seprase, is localized on invadopodia of human malignant melanoma cells. Cancer Res. 54, 5702–5710.

Morimoto C, and Schlossman S F (1994). CD26: A key costimulatory molecule on CD4 memory T cells, Immunologist 2, 4–7.

Mueller, S. C., Ghersi, G., Akiyama, S. K., Sang, Q. X., Howard, L., Pineiro-Sanchez, M., Nakahara, H., Yeh, Y., and Chen, W.-T. (1999). A novel protease-docking function of integrin at invadopodia. J. Biol. Chem. 274, 24947–24952.

Nakahara, H., Howard, L., Thompson, E. W., Sato, H., Seiki, M., Yeh, Y., and Chen, W.-T. (1997). Transmembrane/cytoplasmic domain-mediated membrane type 1-matrix metalloprotease docking to invadopodia is required for cell invasion. Proc. Natl. Acad. Sci. U.S.A. 94, 7959–7964.

Pepper, M. S., Montesano, R., Mandriota, S. J., Orci, L., and Vassalli, J. D. (1996). Angiogenesis: A paradigm for balanced extracellular proteolysis during cell migration and morphogenesis. Enzyme and Protein 49, 138–162.

Pepper, M. S., Sappino, A.-P., Stöcklin, R., Montesano, R., Orci, L., and Vassalli, J.-D. (1993). Upregulation of urokinase receptor expression on migrating endothelial cells. J. Cell Biol. 122, 673–684.

Piazza, G. A., Callanan, H. M., Mowery, J., and Hixson, D. C. (1989). Evidence for a role of dipeptidyl peptidase IV in fibronectin-mediated interactions of hepatocytes with extracellular matrix. Biochem. J. 262, 327–334.

Pineiro-Sanchez, M. L., Goldstein, L. A., Dodt, J., Howard, L., Yeh, Y., Tran, H., Argraves, W. S., and Chen, W.-T. (1997). Identification of the 170-kDa melanoma membrane-bound gelatinase (seprase) as a serine integral membrane protease. J. Biol. Chem. 272, 7595–7601; Correction (1998) J. Biol. Chem. 273, 13366.

Scanlan, M. J., Raj, B. K., Calvo, B., Garin-Chesa, P., Sanz-Moncasi, M. P., Healey, J. H., Old, L. J., and Rettig, W. J. (1994). Molecular cloning of fibroblast activation protein alpha, a member of the serine protease family selectively expressed in stromal fibroblasts of epithelial cancers. Proc. Natl. Acad. Sci. U.S.A. 91, 5657–5661.

Stetler-Stevenson, W. G., Aznavoorian, S., and Liotta, L. A. (1993). Tumor cell interactions with the extracellular matrix during invasion and metastasis. Annu. Rev. Cell Biol. 9, 541–573.

Weidner et al. New England J. of Med. 324:1–8 (1991).

Yaron, A. and Naider, F. (1993). Proline-dependent structural and biological properties of peptides and proteins. Crit. Rev. Biochem. Mol. Biol. 28, 31–81.

Zucker, S., Drews, M., Conner, C., Foda, H. D., DeClerck, Y. A., Langley, K. E., Bahou, W. F., Docherty, A. J., and Cao, J. (1998). Tissue inhibitor of metalloproteinase-2 (TIMP-2) binds to the catalytic domain of the cell surface receptor, membrane type 1-matrix metalloproteinase 1 (MT1-MMP). Journal of Biological Chemistry 273, 1216–1222.

What is claimed is:

1. A continuous cell line which produces a monoclonal antibody which specifically binds an epitope of a human DPPIV (dipeptidyl peptidase IV/CD26) recognized by E19 or E26.

2. The continuous cell line of claim 1 wherein the monoclonal antibody is E19.

3. The continuous cell line of claim 1 wherein the monoclonal antibody is E26.

4. The continuous cell line of claim 2 which is the E19 hybridoma.

5. The continuous cell line of claim 3 which is the E26 hybridoma.

* * * * *

UNITED STATES PATENT AND TRADEMARK OFFICE
CERTIFICATE OF CORRECTION

PATENT NO.    : 6,573,096 B1
DATED         : June 3, 2003
INVENTOR(S)   : Chen

It is certified that error appears in the above-identified patent and that said Letters Patent is hereby corrected as shown below:

Title page,
Item [74], *Attorney, Agent or Firm*, "Hoffman & Baron, LLP" should read
-- Hoffmann & Baron, LLP --

Column 1,
Line 43, "serin-integral membrane roteases (SIMP)...", should read -- serine-integral membrane proteases (SIMP) ... --

Column 4,
Line 49, "(C27, Bloch et al., 19977) ...", should read -- (C27, Bloch et al., 1997) ... --

Signed and Sealed this

Ninth Day of September, 2003

JAMES E. ROGAN
*Director of the United States Patent and Trademark Office*